United States Patent
Saglam et al.

(10) Patent No.: US 10,219,867 B2
(45) Date of Patent: Mar. 5, 2019

(54) REMOTELY-OPERATED ROBOTIC CONTROL SYSTEM FOR USE WITH A MEDICAL INSTRUMENT AND ASSOCIATED USE THEREOF

(71) Applicants: Remzi Saglam, Ankara (TR); Ahmet Sinan Kabakci, Ankara (TR); Erhan Koruk, Ankara (TR)

(72) Inventors: Remzi Saglam, Ankara (TR); Ahmet Sinan Kabakci, Ankara (TR); Erhan Koruk, Ankara (TR)

(*) Notice: Subject to any disclaimer, the term of this patent is extended or adjusted under 35 U.S.C. 154(b) by 649 days.

(21) Appl. No.: 14/190,619

(22) Filed: Feb. 26, 2014

(65) Prior Publication Data

US 2014/0243849 A1 Aug. 28, 2014

Related U.S. Application Data

(60) Provisional application No. 61/769,453, filed on Feb. 26, 2013.

(51) Int. Cl.
*A61B 34/30* (2016.01)
*A61B 18/22* (2006.01)
*A61B 34/00* (2016.01)

(52) U.S. Cl.
CPC .............. *A61B 34/30* (2016.02); *A61B 18/22* (2013.01); *A61B 34/75* (2016.02); *A61B 34/76* (2016.02); *A61B 2018/2238* (2013.01); *A61B 2034/301* (2016.02); *A61B 2218/002* (2013.01)

(58) Field of Classification Search
CPC ..................... A61B 34/30; A61B 2034/301
See application file for complete search history.

(56) References Cited

U.S. PATENT DOCUMENTS

| 5,184,601 A * | 2/1993 | Putman ................. B25J 9/042 312/209 |
| 2002/0120252 A1 * | 8/2002 | Brock .................... A61B 34/20 606/1 |
| 2004/0176751 A1 * | 9/2004 | Weitzner ............ A61B 17/0469 606/1 |
| 2005/0234293 A1 * | 10/2005 | Yamamoto ......... A61B 1/00082 600/102 |
| 2007/0005002 A1 * | 1/2007 | Millman ............. A61M 1/0058 604/30 |

(Continued)

OTHER PUBLICATIONS

Mihir M. Desai, Flexible Robotic Retrograde Renoscopy: Description of Novel Robotic Device and Preliminary Laboratory Experience, 2008, pp. 42-46, Urology 72 (1), U.S.

*Primary Examiner* — Alexander J Orkin
(74) *Attorney, Agent, or Firm* — Ashkan Najafi

(57) ABSTRACT

A manipulator, for use with a robotic control system, to maneuver an existing instrument (e.g., medical instrument) to a desired location within a target zone includes at least one controller, a rotation mechanism in communication with the at least one controller and being rotated about a first axis, a horizontal movement mechanism in communication with the at least one controller and being displaced along a first path, and a deflection mechanism capable of receiving a portion of the existing instrument. Such a deflection mechanism is in communication with the at least one controller and displaced along a second path in such a manner that causes deflection of a distal end (e.g., portion of an insertion tube) of the existing medical instrument.

20 Claims, 26 Drawing Sheets

(56) References Cited

U.S. PATENT DOCUMENTS

| | | | |
|---|---|---|---|
| 2007/0043338 A1* | 2/2007 | Moll | A61B 34/77 606/1 |
| 2007/0060879 A1* | 3/2007 | Weitzner | A61B 17/12045 604/95.04 |
| 2007/0137371 A1* | 6/2007 | Devengenzo | B25J 15/04 74/490.01 |
| 2008/0183193 A1* | 7/2008 | Omori | A61B 17/29 606/130 |
| 2008/0215181 A1* | 9/2008 | Smith | A61B 5/06 700/245 |
| 2008/0234631 A1* | 9/2008 | Reis | A61B 19/2203 604/122 |
| 2011/0028894 A1* | 2/2011 | Foley | A61M 25/0136 604/95.01 |
| 2011/0270273 A1 | 11/2011 | Moll et al. | |
| 2012/0004668 A1 | 1/2012 | Wallace et al. | |

\* cited by examiner

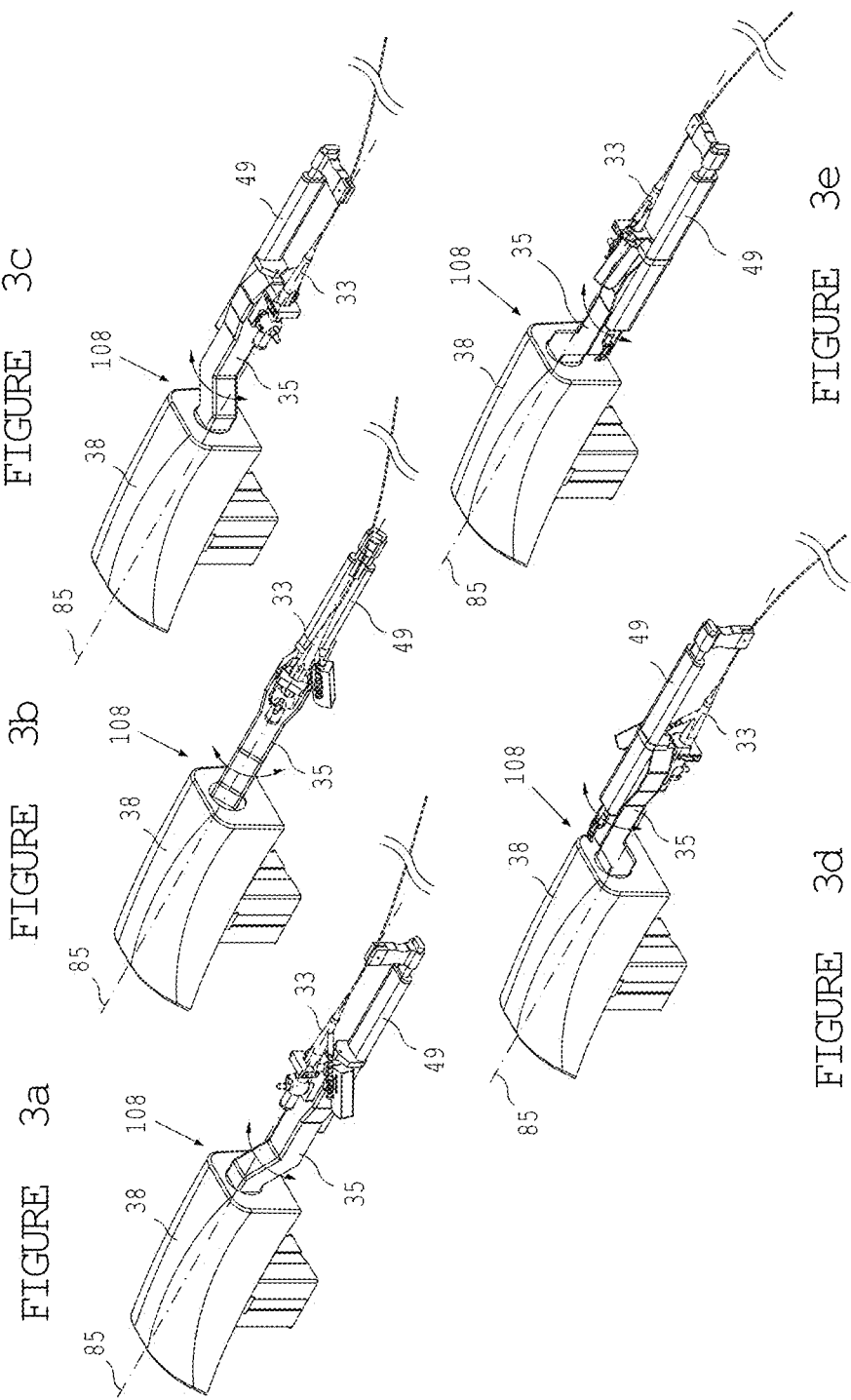

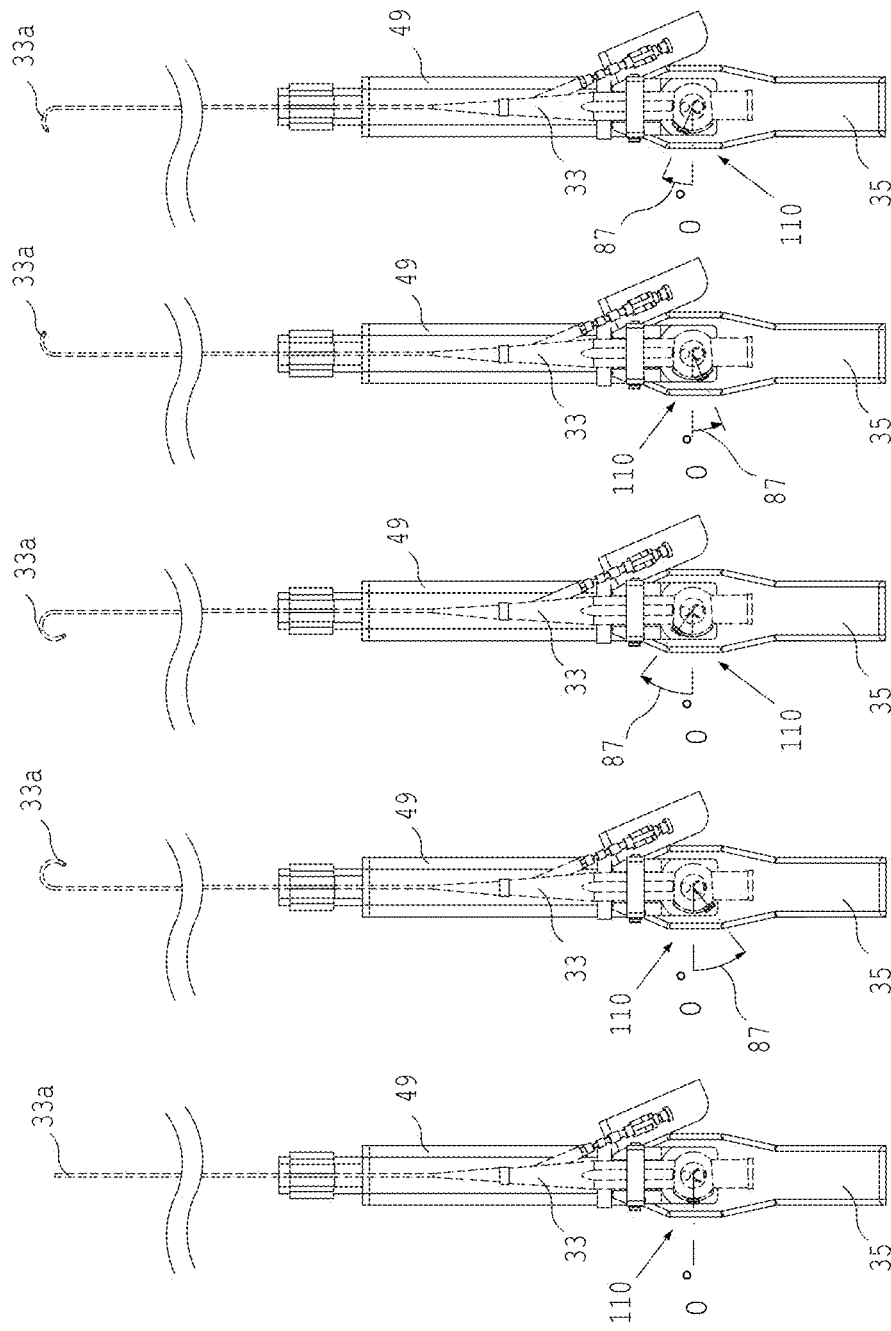

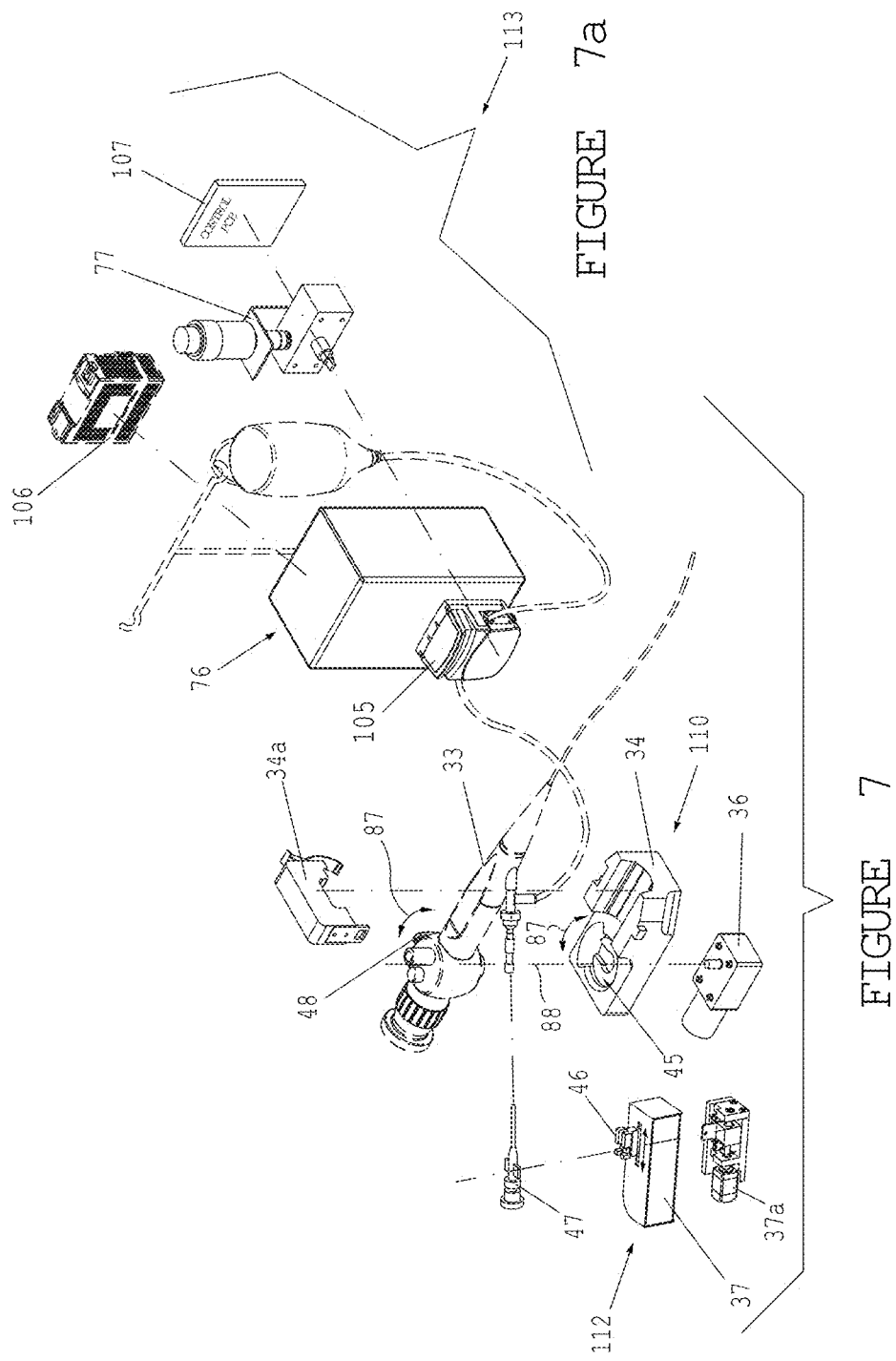

REMOTELY-OPERATED ROBOTIC CONTROL SYSTEM FOR USE WITH A MEDICAL INSTRUMENT AND ASSOCIATED USE THEREOF

CROSS REFERENCE TO RELATED APPLICATIONS

This application claims the benefit of U.S. Provisional Application No. 61/769,453 filed Feb. 26, 2013, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF NON-LIMITING EXEMPLARY EMBODIMENT(S) OF THE PRESENT DISCLOSURE

Technical Field

Exemplary embodiment(s) of the present disclosure relate to robotic control systems and individual components thereof employed in the medical industry and, more particularly, to a remotely-operated robotic control system employing a versatile manipulator to facilitate precise use of an instrument during a procedure.

Prior Art

Generally, there have been attempts to perform a minimally invasive surgical (MIS) procedure. Such MIS procedures are aimed at reducing the amount of extraneous tissue that is damaged during diagnostic or surgical procedures, thereby reducing patient recovery time, discomfort, and deleterious side effects. A common form of such procedures is endoscopy, for example, which is used for minimally invasive inspection and surgery inside the patient's body. To perform such MIS procedures, a surgeon needs a special medical instrument (e.g., flexible uretero-renoscope, flexible endoscope). The surgeon passes such instruments through a small incision of a body wall—or existing orifice—to a surgical site and manipulates the medical instrument from outside the body wall by sliding the medical instrument in and out through the body wall, rotating and pivoting the medical instrument against the body wall.

However, it has been found that a high level of dexterity is required to accurately control such medical instruments. And, the surgeon has no flexibility of tool replacement. Additionally, he or she experiences difficulty in approaching the surgical site through the incision. The length and construction of differing medical instruments reduces the surgeon's ability to feel forces exerted by the surgical site on the medical instruments. Further, human hands typically have at least a minimal amount of tremor. The tremor further increases the difficulty of performing minimally invasive surgical procedures. So, only a relatively small number of MIS procedures have been performed due to limitations in medical instruments, techniques and the surgical training.

U.S. published patent application no. 2012/0004668 discloses a robotic catheter system including a controller with a master input device capable of manipulating a catheter in four directions (i.e., up/down/right/left) during cardiology procedures. As best understood, a U.S. urologist, Dr. Mihir Desai, attempted to employ such a robotic catheter system with a flexible ureterorenoscopy. Dr. Desai used the robotic catheter system to treat swine—pig—kidney stones because the diameter of that catheter was too thick for insertion in to a human urinary system. Unfortunately, Dr. Desai's flexible endoscopy device is homemade and the robotic catheter system is not capable of being employed with conventional—commercially available—flexible ureterorenoscopy devices. Please see applicant's Information Disclosure Statement included herewith for more information regarding Dr. Desai's study.

Furthermore, treatment of large stones takes a relatively long time and requires precise movement on the kidney stone surface. Holding and manipulating the hand-piece of a conventional flexible endoscope and deflection lever is difficult and tiresome during long operations while the surgeon is standing, wearing a lead apron, and holding the endoscope with his/her raised hand. Therefore, surgeons (e.g., urologists) use conventional, manual techniques to treat primarily small kidney stones; infrequently treating large kidney stones.

There exists a continued need for a minimally invasive robotic control system that increase a surgeon's dexterity when working within an internal surgical site as well as to allow a surgeon to perform MIS procedures on a patient by way of, for example, manipulator controlling a medical instrument located at a remote location while monitoring a procedure by way of, for example, viewer which displays an image of the surgical site via a camera. By way of the manipulator employed by the remotely-operated robotic system, the surgeon can manipulate medical instrument movements without directly holding and moving the medical instrument by hand.

BRIEF SUMMARY OF NON-LIMITING EXEMPLARY EMBODIMENT(S) OF THE PRESENT DISCLOSURE

In view of the foregoing background, it is therefore an object of the non-limiting exemplary embodiment(s) to provide a system and method for providing a remotely-operable robotic control system employing a manipulator for use with an instrument (e.g., medical instrument and non-medical instrument). These and other objects, features, and advantages of the non-limiting exemplary embodiment(s) are provided by, inter alia, a robotic manipulator that enables rotation movement and deflection movement of a flexible endoscope as well as horizontal movement of the flexible endoscope and/or the patient. The terms "endoscope," "uretero-renoscope," "fURS," "instrument," "medical instrument" and variations thereof are interchangeably used throughout the present disclosure.

In a non-limiting exemplary embodiment, an object of the present disclosure is to provide a remotely operable manipulator, which controls the flexible endoscope for long durations of time so a surgeon can sit down and remotely control the manipulator from a safe location away from a radiation zone.

In a non-limiting exemplary embodiment, an object of the present disclosure is to provide a precisely controllable manipulator that is capable of operating flexible endoscopes.

In a non-limiting exemplary embodiment, an object of the present disclosure is to insert an auxiliary instrument (e.g., laser fiber, etc.) through a working channel of a flexible endoscope, which can be used during precise treatment procedures by either fixing or actuating in/out movements of the auxiliary instrument.

In a non-limiting exemplary embodiment, an object of the present disclosure is to provide a precise movement of a distal end of a flexible endoscope by precisely controlling a manipulator, which actuates a deflection movement of the flexible endoscope.

In a non-limiting exemplary embodiment, an object of the present disclosure is to provide a precise rotation movement of a manipulator, which simulates a rotational speed of the user while controlling the manipulator rotation (i.e. the user controls the rotation of the flexible endoscope by rotating the handle on the control console; when he/she rotates the handle fast, the robotic manipulator rotates the flexible endoscope at a commensurate speed (e.g., fast), when he/she slowly and precisely rotates the handle, the flexible endoscope is rotated slowly and precisely).

In a non-limiting exemplary embodiment, an object of the present disclosure is to provide horizontal movement for insertion and/or retraction of a flexible endoscope shaft in the body of a patient according to an adjustable user speed input at the control console. In this manner, a higher speed user input causes faster movement of the flexible endoscope and a slower speed user input causes slower, precise movement of the flexible endoscope.

In a non-limiting exemplary embodiment, an object of the present disclosure is to provide a control console that enables a user to maneuver the manipulator for positioning the flexible endoscope inside the body to reach and treat a kidney stone, for example.

In a non-limiting exemplary embodiment, an object of the present disclosure is to provide a manipulator that has the ability to sense friction and excessive load at a distal tip of thereof. Because flexible endoscopes are tendon actuated devices, it is desirable for the manipulator to apply torque to its deflection mechanism (e.g., lever, etc.) of the flexible endoscope. Furthermore, because tendons of the flexible endoscope are fragile, the applied force to the deflection mechanism can be evaluated. Therefore, the sense of any excessive tension is informed to the user (e.g., the user can see or feel that tension) and/or the torque is limited by the manipulator to avoid damage to the flexible endoscope.

In a non-limiting exemplary embodiment, an object of the present disclosure is to provide an instrument holder at the robot manipulator that is adaptable to different conventional brands/models of flexible endoscopes (e.g., variety of brands/models of flexible endoscopes can be connected to the manipulator and used for treatment).

In a non-limiting exemplary embodiment, an object of the present disclosure is to provide a system controller (e.g., control unit) having associated software instructions to automatically perform pre-defined movements according to the user's request. Such pre-defined movements provide, for example, a desired endoscope position after executing a predetermined rotational movement; a desired laser fiber insertion position after executing a predetermined deflection movement; a desired initial laser fiber position; a desired laser fiber firing position; and initial and middle positions after executing a predetermined horizontal movement. In other words, the manipulator can automatically return the instrument to a desired pre-determined starting, intermediary and/or final position, as identified by user input.

In a non-limiting exemplary embodiment, an object of the present disclosure is to provide user controls that remotely execute all maneuvers of the flexible endoscope regardless of whether the control console is in remote, direct, indirect and/or wired communication with the manipulator.

In a non-limiting exemplary embodiment, an object of the present disclosure is to provide a robotic manipulator that is capable of controlling in/out movements of laser fiber operably seated inside a working channel of a conventional flexible endoscope. As understood by one-skilled in the art, if the tip of the laser fiber is located inside the working channel and the laser is fired, then the working channel will be perforated and the endoscope will malfunction. If the tip of the laser fiber is very close to the distal end of the flexible endoscope and the laser is fired, then the optic end of the endoscope will be damaged. Advantageously, the control console checks a real-time position of the laser fiber tip and inhibits laser firing if the tip of the laser fiber is close to the distal end of flexible endoscope. In this manner, operational safe guards are provided to protect the flexible endoscope from premature and undesirable damage, thereby prolonging its useful life.

In a non-limiting exemplary embodiment, an object of the present disclosure is to provide a manipulator having an irrigation pump actuating mechanism that discharges liquid used during endoscopic procedure. A controller at the manipulator adjusts the pumping speed according to the user input at the control console. The user can adjust a flow rate of the liquid for achieving better vision from the camera of the endoscope. In addition, the irrigation pump has a flush feature which provides an instantaneous maximum flow rate.

In a non-limiting exemplary embodiment, an object of the present disclosure is to provide alternate deflection mechanisms that are retrofitted to interface with a U.S.-type as well as a European-type flexible endoscope. Thus, the manipulator is transformable to operably control EU and US endoscopes. In addition, software changes are provided for properly interfacing the control console with the manipulator according to the type of endoscope employed (e.g., US, EU, manufacturer-specific, etc.). Of course, the control console, software and manipulator may be further modified to operably interface with a variety of conventional flexible endoscope employed in various regions of the world, not limited to US and EU endoscopes.

In a non-limiting exemplary embodiment, an object of the present disclosure is to provide faster and more effective treatment by programming (e.g., automated) predefined movements via software instructions. For example, such predefined movements may include: painting, dusting and pop-corning methods of treating kidney stones.

In a non-limiting exemplary embodiment, an object of the present disclosure is to provide software instructions that automatically and synchronously adjust a position of the manipulator relative to a temporary (e.g., dynamic) position of the kidney stone(s) as the patient inhales/exhales.

In a non-limiting exemplary embodiment, an object of the present disclosure is to provide software instructions that automatically measures and learns a rotational angle of the flexible endoscope while controlled by the manipulator, wherein such a learned rotational angle is overlaid or superimposed, for example, on the video monitor during the procedure. In this manner, the surgeon (e.g., operator) is able to learn real-time angular rotations of the manipulator without interrupting the procedure.

There has thus been outlined, rather broadly, the more important features of non-limiting exemplary embodiment(s) of the present disclosure so that the following detailed description may be better understood, and that the present contribution to the relevant art(s) may be better appreciated.

There are additional features of the non-limiting exemplary embodiment(s) of the present disclosure that will be described hereinafter and which will form the subject matter of the claims appended hereto.

BRIEF DESCRIPTION OF THE NON-LIMITING EXEMPLARY DRAWINGS

The novel features believed to be characteristic of non-limiting exemplary embodiment(s) of the present disclosure are set forth with particularity in the appended claims. The non-limiting exemplary embodiment(s) of the present disclosure itself, however, both as to its organization and method of operation, together with further objects and advantages thereof, may best be understood by reference to the following description taken in connection with the accompanying drawings in which:

FIGS. 3a-3e are perspective views illustrating rotational movement of the manipulator as it rotates the instrument about a first axis (e.g., x-axis);

FIGS. 4a-4e are top plan views illustrating deflectional movement of the manipulator for causing deflection at a distal end of the instrument;

FIGS. 7-7a are enlarged, exploded views illustrating the interrelationship between portions of the deflection mechanism, irrigation pump actuating mechanism and auxiliary instrument actuating mechanism located at the manipulator;

Figure 2:
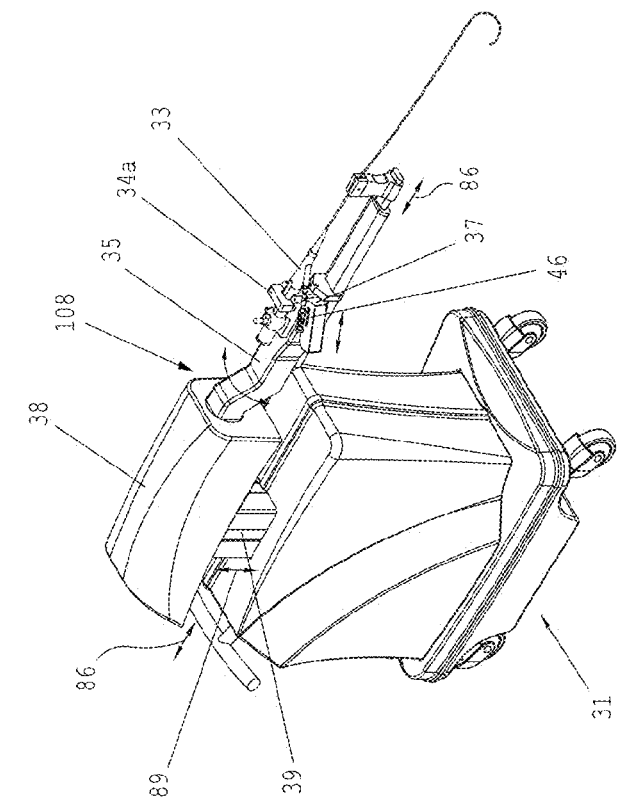
FIG. 2 is a perspective view illustrating a front side of a robotic manipulator in communication with the control unit shown in FIG. 1 and for maneuvering an instrument in response to the operator input, in accordance with a non-limiting exemplary embodiment of the present disclosure.
Figure 1:
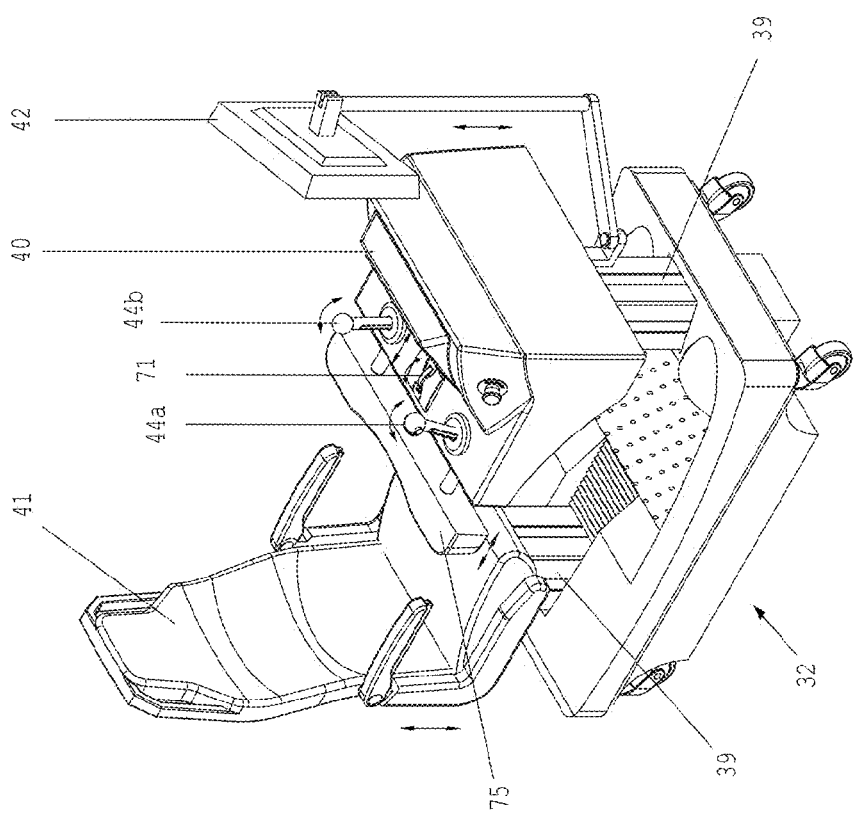
FIG. 1 is a perspective view illustrating a front side of a control unit, employed by a robotically-operated control system, for receiving an operator input, in accordance with a non-limiting exemplary embodiment of the present disclosure.
Figure 6:
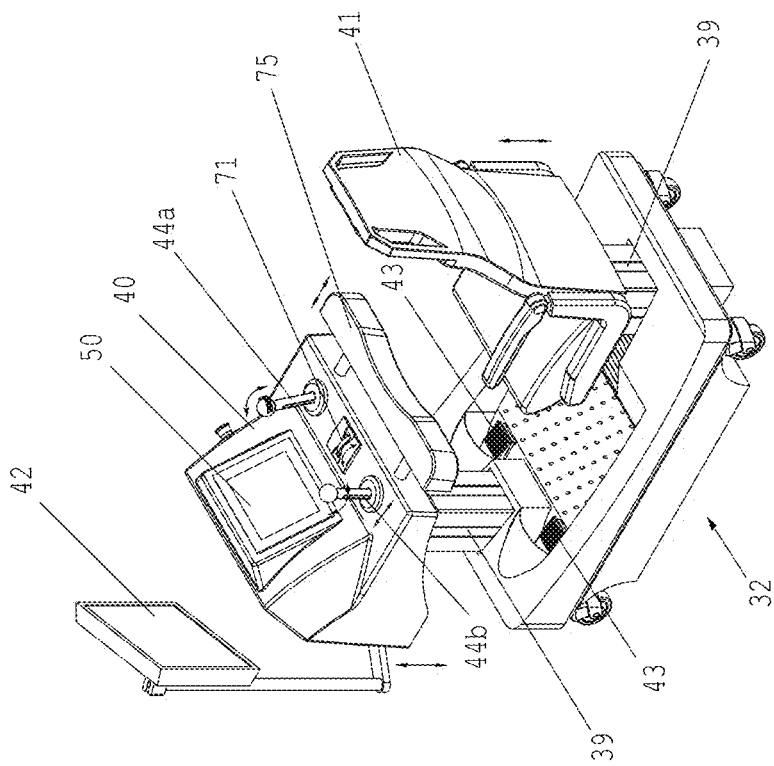
FIG. 6 is a perspective view illustrating an operator's control console at the control unit shown in FIG. 1.
Figure 5:
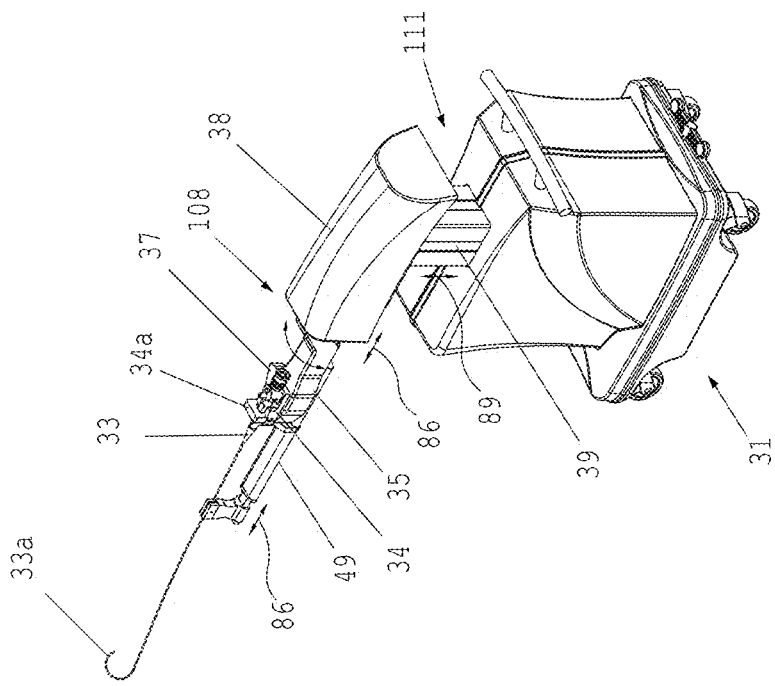
FIG. 5 is a perspective view illustrating a rear side of the manipulator shown in FIG. 2.
Figure 8:
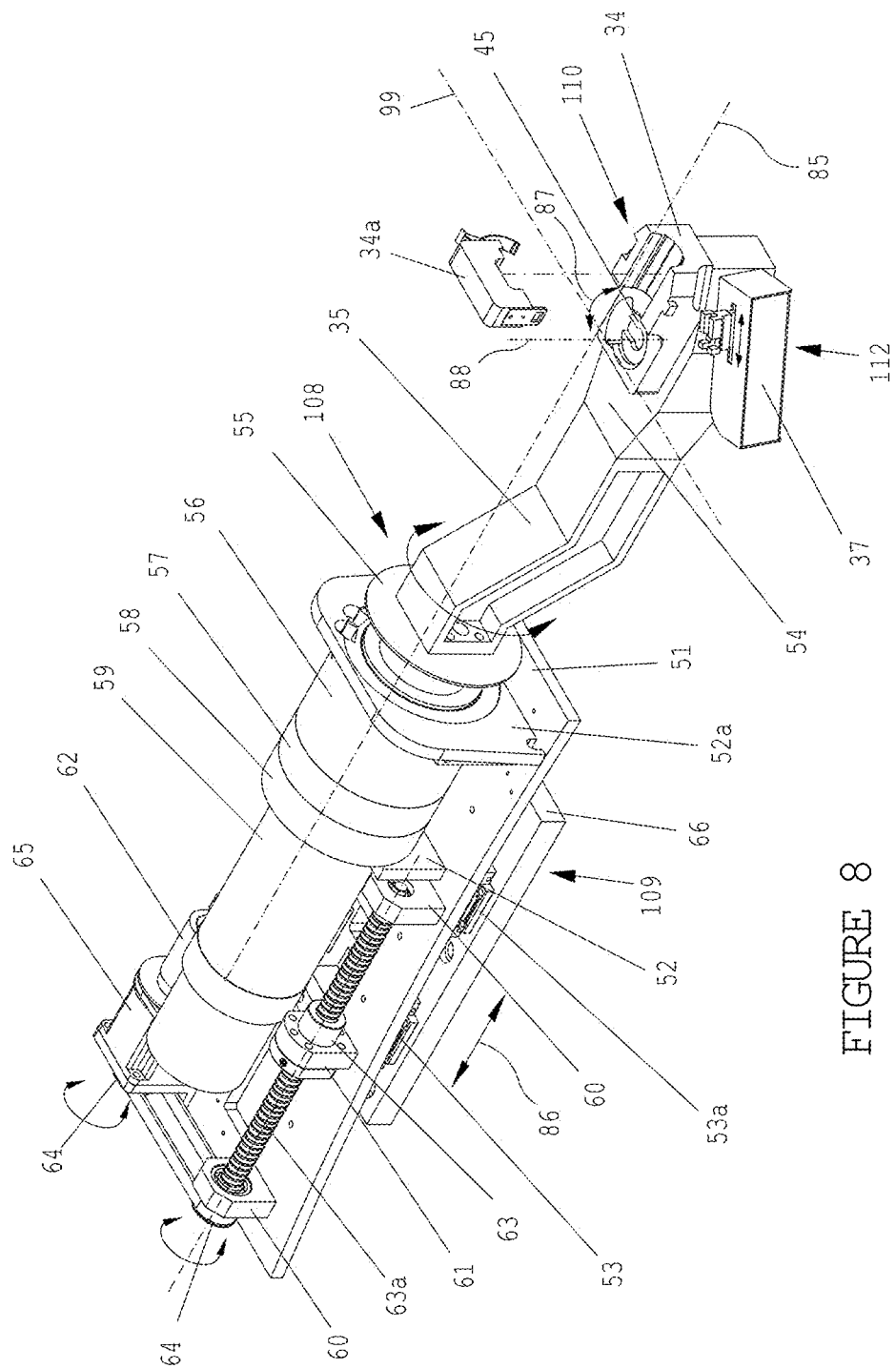
FIG. 8 is an enlarged perspective view of a portion of the manipulator illustrating the rotational, horizontal and deflection movements with reference to an x-axis (e.g., first), y-axis (e.g., second) and z-axes.
Figure 9:
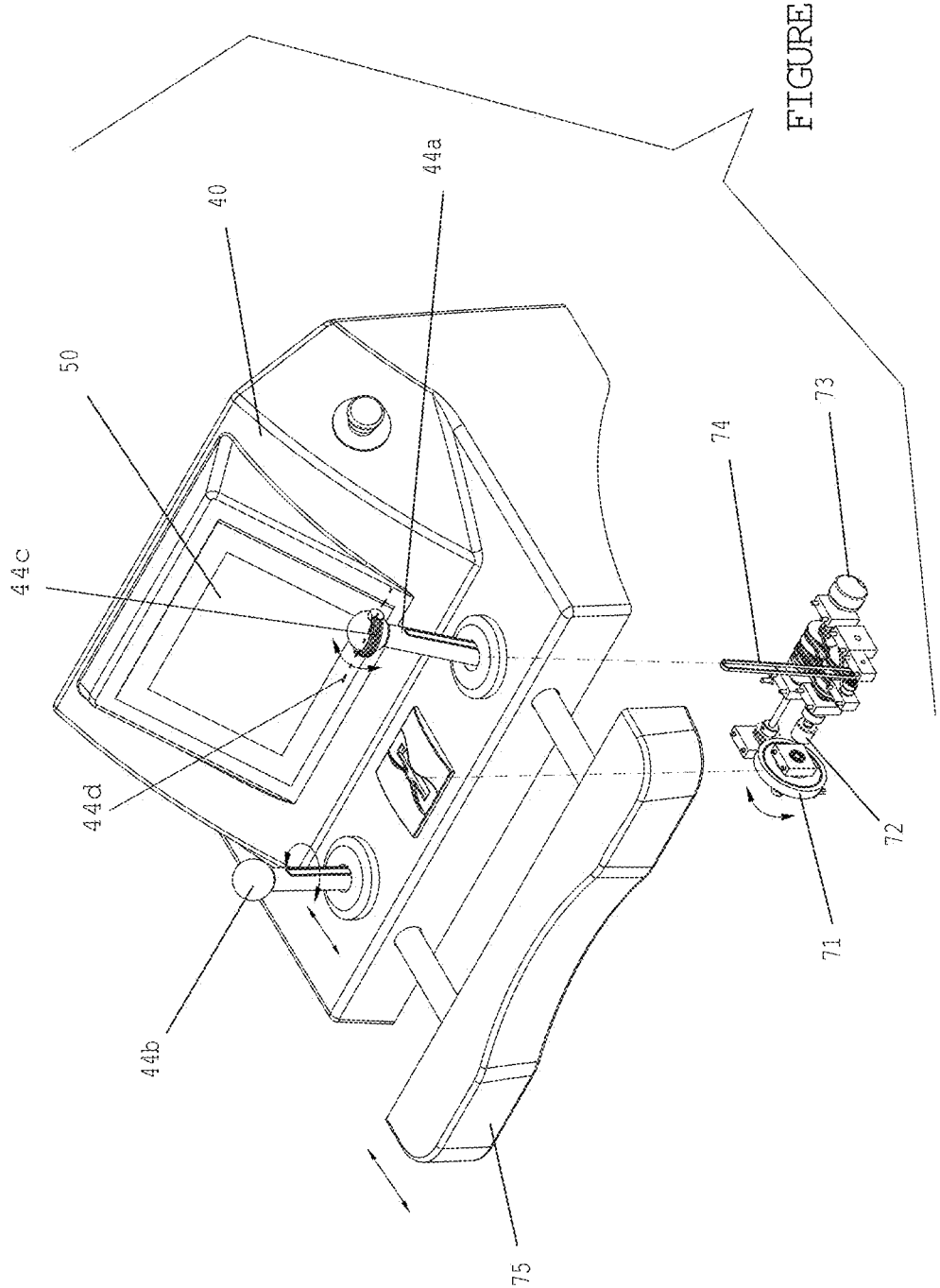
FIG. 9 is an enlarged exploded view of a portion of the control console illustrating the control handles and associated gear mechanism for providing realistic (e.g., haptic) feedback while maneuvering the instrument.
Figure 10:
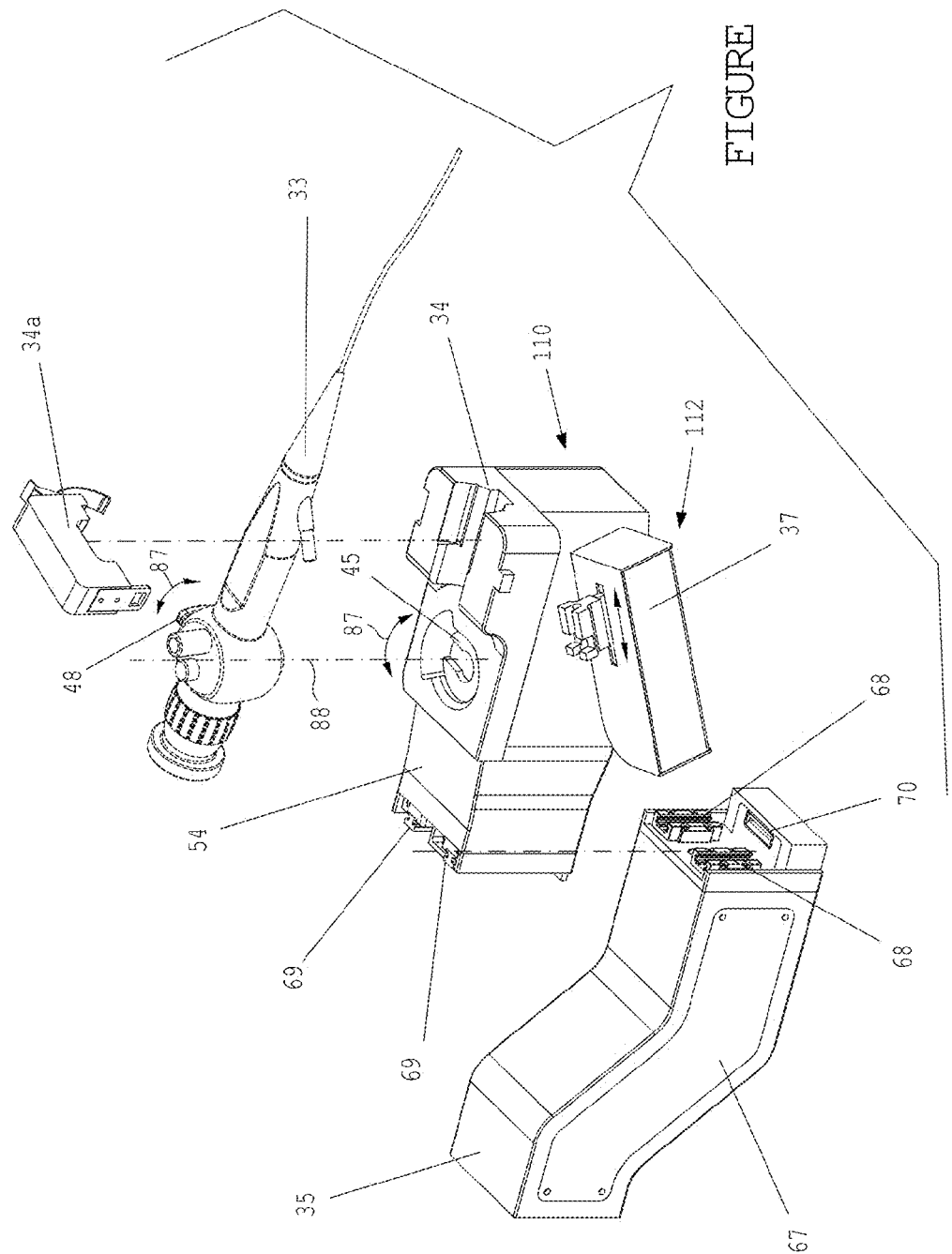
FIG. 10 is an enlarged, exploded view illustrating the interrelationship between the rotation arm, endoscope fixing attachment, deflection mechanism, and interchangeable endoscope holder (e.g., according to different brands of endoscopes)
Figure 11:
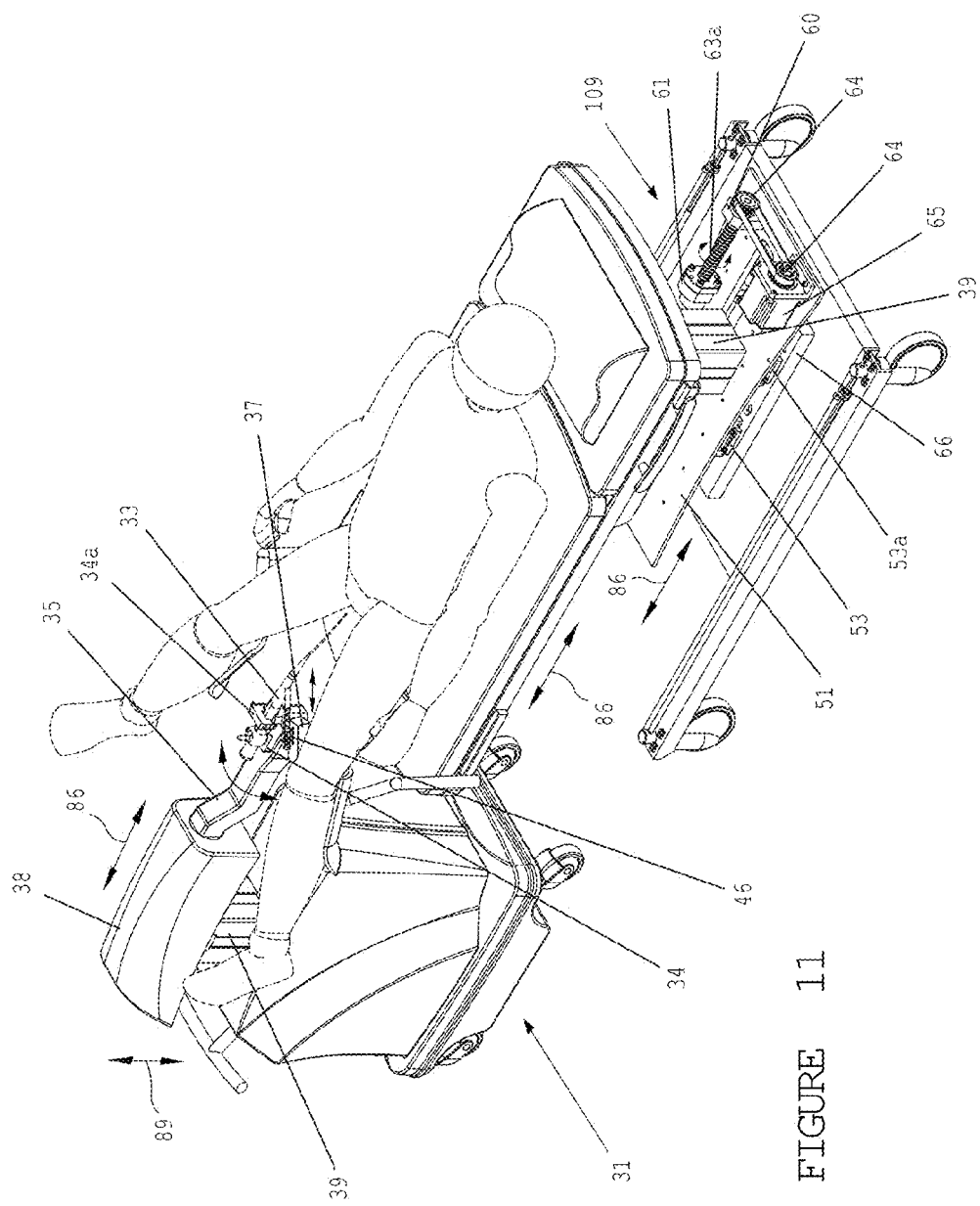
FIG. 11 is a perspective view illustrating the interrelationship between the manipulator and a patient bed wherein horizontal movement may be actuated at the manipulator and/or patient bed.

Those skilled in the art will appreciate that the figures are not intended to be drawn to any particular scale; nor are the figures intended to illustrate every non-limiting exemplary embodiment(s) of the present disclosure. The present disclosure is not limited to any particular non-limiting exemplary embodiment(s) depicted in the figures nor the shapes, relative sizes or proportions shown in the figures.

DETAILED DESCRIPTION OF NON-LIMITING EXEMPLARY EMBODIMENT(S) OF THE PRESENT DISCLOSURE

The present disclosure will now be described more fully hereinafter with reference to the accompanying drawings, in which non-limiting exemplary embodiment(s) of the present disclosure is shown. The present disclosure may, however, be embodied in many different forms and should not be construed as limited to the non-limiting exemplary embodiment(s) set forth herein. Rather, such non-limiting exemplary embodiment(s) are provided so that this application will be thorough and complete, and will fully convey the true spirit and scope of the present disclosure to those skilled in the relevant art(s).

The illustrations of the non-limiting exemplary embodiment(s) described herein are intended to provide a general understanding of the structure of the present disclosure. The illustrations are not intended to serve as a complete description of all of the elements and features of the structures, systems and/or methods described herein. Other non-limiting exemplary embodiment(s) may be apparent to those of ordinary skill in the relevant art(s) upon reviewing the disclosure. Other non-limiting exemplary embodiment(s) may be utilized and derived from the disclosure such that structural, logical substitutions and changes may be made without departing from the true spirit and scope of the present disclosure. Additionally, the illustrations are merely representational are to be regarded as illustrative rather than restrictive.

One or more embodiment(s) of the disclosure may be referred to herein, individually and/or collectively, by the term "non-limiting exemplary embodiment(s)" merely for convenience and without intending to voluntarily limit the true spirit and scope of this application to any particular non-limiting exemplary embodiment(s) or inventive concept. Moreover, although specific embodiment(s) have been illustrated and described herein, it should be appreciated that any subsequent arrangement designed to achieve the same or similar purpose may be substituted for the specific embodiment(s) shown. This disclosure is intended to cover any and all subsequent adaptations or variations of other embodiment(s). Combinations of the above embodiment(s), and other embodiment(s) not specifically described herein, will be apparent to those of skill in the relevant art(s) upon reviewing the description.

References in the specification to "one embodiment(s)", "an embodiment(s)", "a preferred embodiment(s)", "an alternative embodiment(s)" and similar phrases mean that a particular feature, structure, or characteristic described in connection with the embodiment(s) is included in at least an embodiment(s) of the non-limiting exemplary embodiment(s). The appearances of the phrase "non-limiting exemplary embodiment" in various places in the specification are not necessarily all meant to refer to the same embodiment(s).

Directional and/or relationary terms such as, but not limited to, left, right, nadir, apex, top, bottom, vertical, horizontal, back, front and lateral are relative to each other and are dependent on the specific orientation of an applicable element or article, and are used accordingly to aid in the description of the various embodiment(s) and are not necessarily intended to be construed as limiting.

The non-limiting exemplary embodiment(s) is/are referred to in FIGS. 1-22 and is/are intended to provide a robotic manipulator 31 for controlling a flexible ureterorenoscope 33 (referred to hereinafter as "fURS"), which enables the urologist to pass a distal end 33a (e.g., distal portion of an insertion tube) of the fURS 33 into a patient's body from the patient's urethra and to reach each calyx of the kidney. Because conventional flexible endoscopes 33 have a working channel, it is possible to treat (e.g., endoscopy) as well as diagnosis (e.g., fluoroscopy) kidney stones, for example. By accessing the working channel with a laser fiber, it is possible to fragment the kidney stones. It should be understood that the exemplary embodiment(s) may be used to operate (e.g., remotely and/or locally) many different types of medical instruments used in a variety of medical procedures, and should not be limited to any particular medical instrument described herein.

LIST OF REFERENCE NUMERALS
ILLUSTRATED IN FIGS. 1-22

30 Remotely-operable fURS system
31 Robotic manipulator
32 Control unit
33 Flexible endoscope
33a Distal tip of flexible endoscope (part of insertion tube)
34 Flexible endoscope fixing attachment
34a Flexible endoscope fixing clamp
35 Bent arm for rotation part of robot
36 Deflection actuator for manipulating a deflection of the distal end of the flexible endoscope
37 Laser fiber actuator
37a Laser fiber actuator components
38 Actuator block for insertion movement (horizontal movement) and rotation movement
39 Vertical lifting (up/down) column
40 Control Console
41 Height adjustable seat
42 Video monitor
43 Foot pedals (e.g., two pieces)
44 Control handles (handles for rotation/insertion 44b and deflection 44a movements)
44c Deflection lever
44d Deflection lever rotation (fulcrum) axis
45 Deflection lever coupler of deflection actuator
46 Holder for fiber fixing adapter
47 Sterile laser fiber fixing adapter
48 Deflection lever of flexible endoscope
49 Length adjustable telescopic fixing rod to prevent bending of proximal part of flexible endoscope
50 Touch panel interface for operator control
51 Upper base plate for horizontal movement
52 Carrying plates for rotation actuator
52a Carrying plates for rotation actuator
53 Linear bearing for horizontal movement
53a Linear bearing for horizontal movement
54 Interchangeable body of flexible endoscope holder for different brands (e.g., KARL STORZ™, RICHARD WOLF™, OLYMPUS™, etc.)
55 Flange for bent arm for rotation part
56 Bearing system for rotation movement
57 Zero backlash speed reducer
58 Flange for rotation motor
59 Rotation motor
60 Bearing assembly for ball screw system
61 Flange for ball screw nut fixed to lower plate
62 Assembly for rotation feedback sensor
63 Ball screw nut for horizontal movement
63a Ball screw for horizontal movement
64 Belt and pulley for horizontal movement
65 Stepper motor for horizontal movement
66 Lower plate for horizontal movement
67 Cover for bent arm for protecting the electronic components
68 Linear bearing—slide
69 Inner part of linear slide
70 Connector for signals of deflection actuator and laser fiber actuator
71 Wheel for precision deflection control
72 Sensor for deflection control
73 Electro-magnetic brake for deflection tension feeling (e.g., resistance)
74 Timing belt for deflection lever control
75 Adjustable arm rest
76 Irrigation pump
77 Irrigation pump actuator
78 Rotation Handle Sensor
79 Horizontal movement handle sensor
80 Controller for control console
81 Chair console distance sensor
82 Chair position sensor
83 Control console table position sensor
85 First axis
86 First path
87 Second path
88 Second axis
89 Third path
90 Controller for manipulator
91 Rotation angular position sensor 92 Deflection torque sensor
93 Deflection angular position sensor
94 Horizontal position sensor
95 Horizontal min-max position sensors
96 Laser fiber driver position sensor
97 Laser fiber driver min-max position sensors
98 Vertical movement position sensor
99 Z-axis
105 Irrigation pump head
106 Irrigation pump power source
107 Irrigation pump printed circuit board (I/O interface)
108 Rotation mechanism
109 Horizontal movement mechanism
110 Deflection mechanism
111 Vertical movement mechanism
112 Laser fiber actuating mechanism
113 Irrigation pump actuating mechanism With reference initially to FIGS. 1-11 and 22, in a non-limiting exemplary embodiment, a manipulator 31 for maneuvering an existing instrument 33 to a desired location within a target zone is disclosed. Such a manipulator 31 includes at least one controller 90, a rotation mechanism 108 in communication with the at least one controller 90 and being rotated about a first axis 85 (e.g., x-axis); a horizontal movement mechanism 109 in communication with the at least one controller 90 and being displaced along a first path 86; and a deflection mechanism 110 capable of receiving a portion of the existing instrument 33. Such a deflection mechanism 110 is in communication with the at least one controller 90 and is thereby displaced along a second path 87. In this manner, displacement of the deflection mechanism 110 along the second path 87 causes deflection of a distal end 33a of the existing medical instrument 33.

In a non-limiting exemplary embodiment, a robotic control system 30 for maneuvering an existing medical instrument 33 to a desired location within a target zone during a medical procedure is disclosed. Such a robotic control system 30 includes a control unit 32 capable of receiving an operator input, and a manipulator 31 in communication with the control unit 32 and responsive to the operator input. The manipulator 31 includes at least one controller 90, a rotation mechanism 108 in communication with the at least one controller 90 and being rotated about a first axis 85 (e.g., x-axis), a horizontal movement mechanism 109 in communication with the at least one controller 90 and being displaced along a first path 86, and a deflection mechanism 110 capable of receiving a portion of the existing instrument 33. Such a deflection mechanism 110 is in communication with the at least one controller 90 and is thereby displaced along a second path 87. In this manner, displacement of the deflection mechanism 110 along the second path 87 causes deflection of a distal end 33a of the existing medical instrument 33.

In a non-limiting exemplary embodiment, the second path 87 is a second axis 88 registered substantially perpendicular to the first axis 85.

In a non-limiting exemplary embodiment, the first path 86 is linear and registered substantially parallel to the first axis 85.

In a non-limiting exemplary embodiment, the first path 86 is non-overlapping and mutually exclusive of the second path 87.

In a non-limiting exemplary embodiment, the deflection mechanism 110 is independently operable from each of the horizontal movement mechanism 109 and the rotation mechanism 108. For example, an operator can chronologically (separately) maneuver the medical instrument 33 along a plurality of sequential directions.

In a non-limiting exemplary embodiment, the deflection mechanism 110 is contemporaneously operable with each of the horizontal movement mechanism 109 and the rotation mechanism 108. For example, an operator can simultaneously maneuver the medical instrument 33 along a plurality of directions.

In a non-limiting exemplary embodiment, the first axis 85 is an x-axis and the second axis 88 is a y-axis, wherein the second path 87 has an arcuate curvature defined about the second axis (e.g., y-axis) along a plane parallel to a z-axis 99.

In a non-limiting exemplary embodiment, the robotic control system 30 further includes a vertical movement mechanism 111 in communication with the at least one controller 90 and configured to raise and lower the rotation mechanism 108 and the deflection mechanism 110 along a third path 89 registered substantially orthogonal to the first path 86.

In a non-limiting exemplary embodiment, the robotic control system 30 further includes an auxiliary instrument actuating mechanism 112 in communication with the at least one controller 90 and attached to the deflection mechanism 110 and located proximate to the horizontal movement mechanism 109. The auxiliary instrument actuating mechanism 112 may control, for example, a laser fiber, a basket catheter, forceps, a grasper, a biopsy catheter, and electrode catheter.

In a non-limiting exemplary embodiment, robotic control system 30 further includes an irrigation pump actuating mechanism 113 in communication with the control unit 32 and being responsive to user input for selectively discharging fluid into a working channel of the existing medical instrument 33.

The present disclosure further includes a method of utilizing a robotic control system 30 for maneuvering an existing medical instrument 33 to a desired location within a target zone during a medical procedure. Such a method includes the initial steps of: obtaining a control console 32 capable of receiving an operator input; and obtaining and communicating a manipulator 31 with the control console 32 wherein the manipulator 31 is responsive to the operator input. Such a manipulator 31 includes at least one controller 90, a rotation mechanism 108 in communication with the at least one controller 90 and being rotated about a first axis 85 (e.g., x-axis), a horizontal movement mechanism 109 in communication with the at least one controller 90 and being displaced along a first path 86, and a deflection mechanism 110 capable of receiving a portion of the existing instrument 33 wherein the deflection mechanism 110 is in communication with the at least one controller 90 and is displaced along a second path 87. The method further includes the step of displacing the deflection mechanism 110 along the second path 87 thereby causing deflection of a distal end 33a of the existing medical instrument 33.

Figure 21:
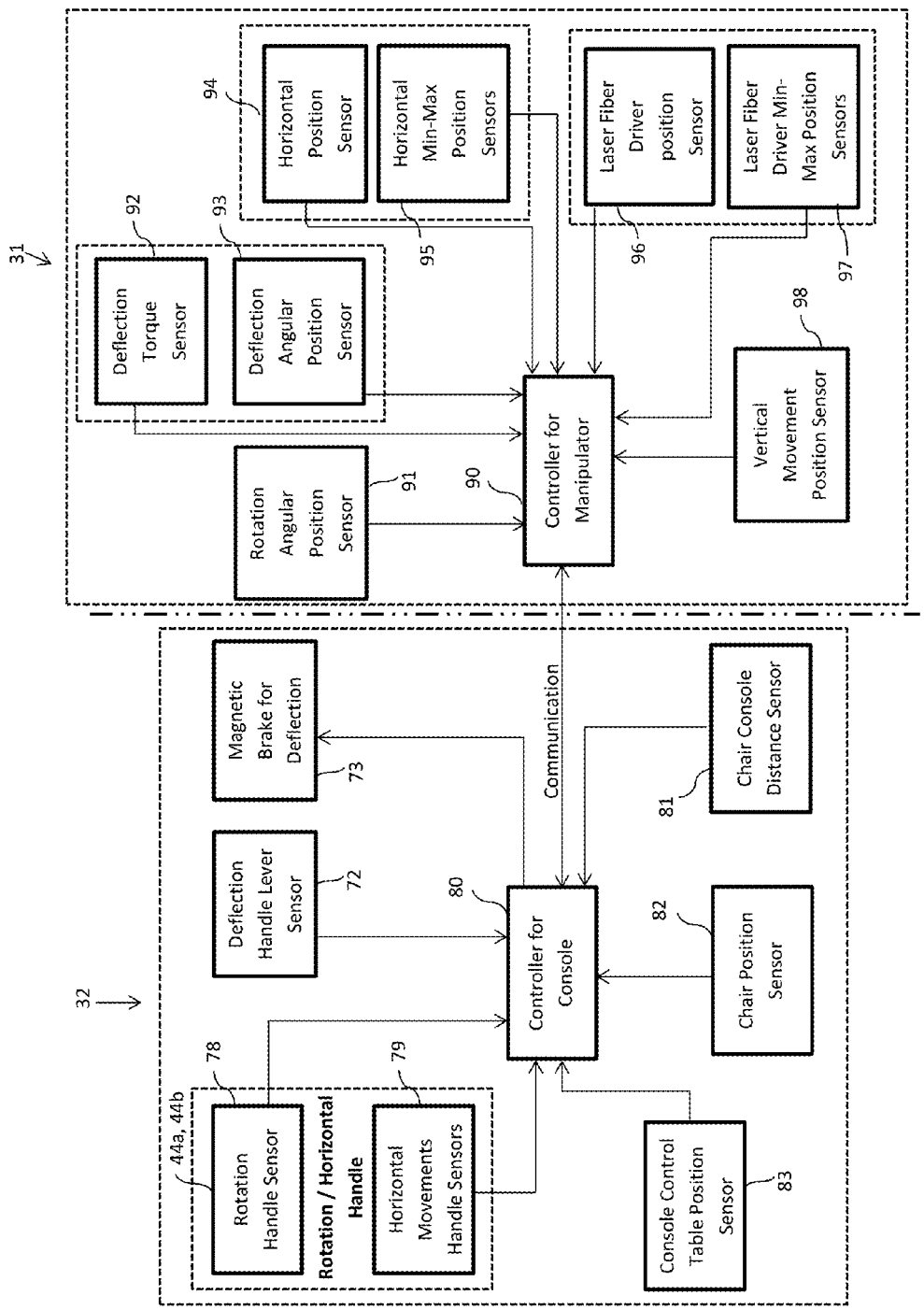
FIG. 21 is a high-level block diagram illustrating the interrelationship between the sensors and respective controller(s) located at the control console and manipulator, respectively.
Figure 22:
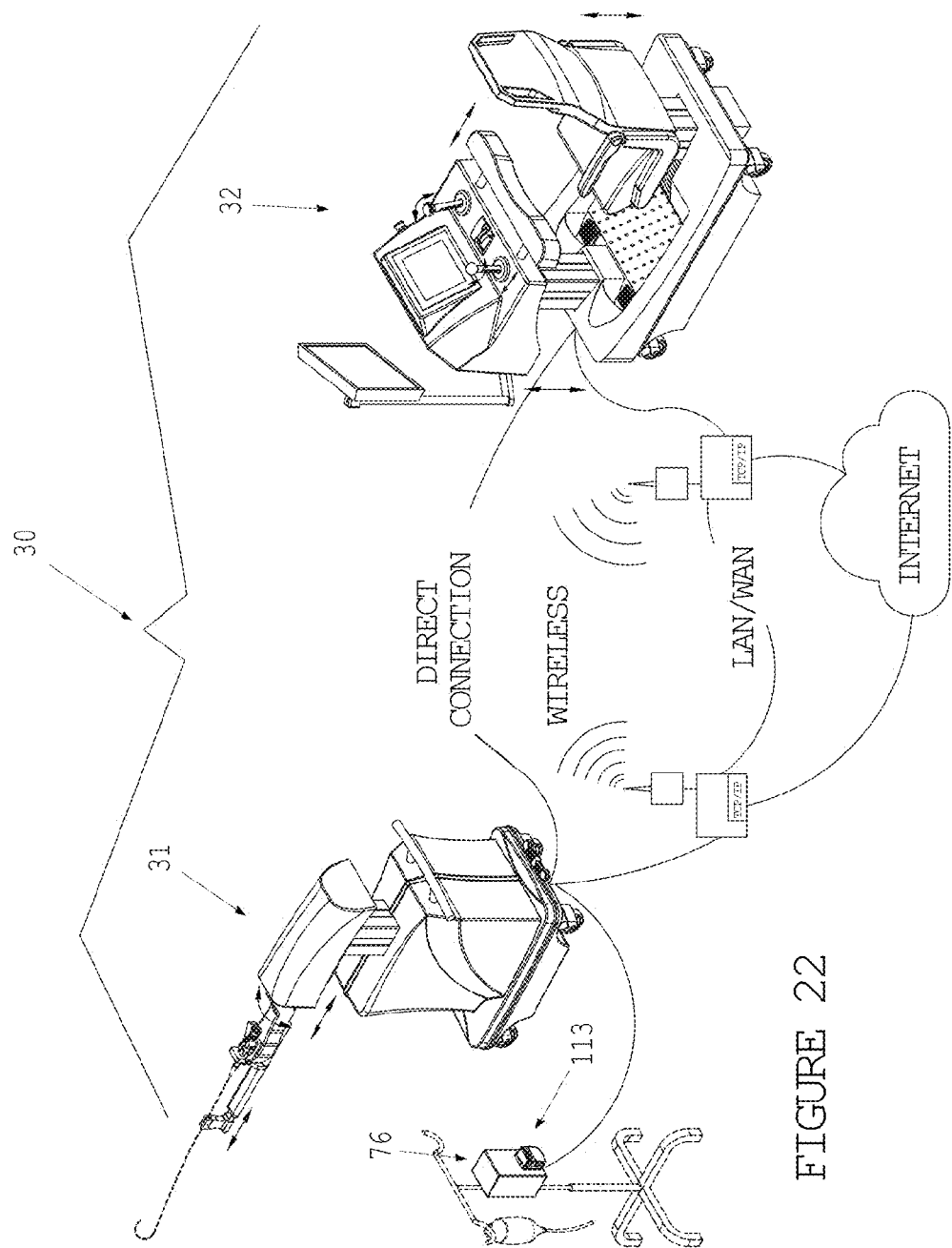
FIG. 22 is schematic diagram illustrating various communication links for communicating the control console to the manipulator.

Referring to FIG. 21, a high-level block diagram of system 30 illustrates the interrelationship between sensors and a respective controller(s) at the control console 32 and manipulator 31, respectively. For example, at control unit 32, sensors 72, 78-79, 81-83 are in communication with controller 80. At manipulator 31, sensors 91-98 are in communication with controller 90. Such aforementioned sensors may include one or more sensor(s), such as a motion and/or pressure sensor(s) may be provided to cause the present disclosure to detecting an event (e.g., manipulator 31 movement). Active and/or passive sensors may be used to react to detectable subject matter such as objects, light, noise, pressure, torque, speed, radiation (e.g., heat), or changes in emitted energy, fields or beams. However, the disclosure is not limited to employing a particular type of sensor. Those skilled in the art will appreciate that other sensors may be used without departing from the scope of the disclosure. Examples of such other sensors include pressure sensitive mats; optical sensors configured to sense light; microwave sensors that use a Gunn diode operating within pre-set limits to transmit/flood a designated area/zone with an electronic field whereby movement in the zone disturbs the field and sets off an alarm; an ultrasonic sensor configured to react to a determined range of ultrasonic sound energy in a protected area; or any other sensor capable of providing motion detection capability in accordance with principles of the disclosure.

Referring again to FIGS. 1-11, in a non-limiting exemplary embodiment, the system 30 includes a robotic manipulator 31 and a control unit 32 remotely maneuvering a commercially available flexible endoscope 33. The flexible endoscope 33 is attached to the robotic manipulator 31 by a fixing attachment 34a (e.g., fastener). The central axis of the flexible endoscope 33 and the rotation axis of the bent arm 35 (e.g., non-linear) for actuator part 35 of manipulator 31 are concentrically aligned. Bent arm 35 enables the surgeon to rotate the flexible endoscope 33 in its own axis (e.g., first axis, x-axis), passing through a center of a hand piece to the shaft of the fURS 33. In this manner, manipulator 31 may be a cylindrical robot.

In a non-limiting exemplary embodiment, a precise motor 36 manipulates deflection of the distal end 33a of the flexible endoscope 33. Such a motor 36 controls flexible endoscope 33 by a lever coupler 45 and it is realistically (e.g., real-time same speed, tension/friction control) controlled by user handle 44a. On that handle 44a, there is a lever 44c similar to the one 48 on the endoscope 33. Such a lever 44c may be pivoted via the user's thumb or other metacarpal, for example. It is noted that handle 44a is statically offset from a vertical axis wherein handle 44a travels generally towards the console 40. Such an offset orientation of handle 44a provides ergonomic benefits but is not critical to actuating deflection movements at lever 44c. The user controls that lever 44c with his/her thumb to make the deflection movement (articulation) of the flexible endoscope distal end 33a (e.g., distal portion of the insertion tube).

In a non-limiting exemplary embodiment, when the user rotates (e.g., pivots) the lever 44c about axis 44d (e.g., +/−45 degrees) on the handle 44a, such pivotal movement is transferred to the control sensor 72 by a timing belt 74. In particular, controlled rotational movement (e.g., spinning) of a pulley of timing belt 74 provides real-time and realistic feedback (e.g., haptic feedback) to the user operating lever 44c. Sensors 92, 93 detect the external force acting on the distal tip 33a and provide real-time feedback to the manipulator 31. In other words, to give a sense of touch to the user, rotation of timing belt 74 pulley is controlled by an electromagnetic brake 73 thereby providing a feeling of friction (e.g., frictional resistance) when the distal tip 33a of the flexible endoscope 33 engages a tissue or an object, for example, during the procedures.

In a non-limiting exemplary embodiment, the precise control of the deflection is enabled by a wheel 71 placed at the middle of the control console 40. Wheel 71 may be calibrated to cause the distal tip 33a of endoscope 33 to deflection approximately +/−270 degrees when deflection lever 44c is pivoted about axis 44d approximately +/−45 degrees. Of course, wheel 71 may be modified to alternate calibrations so that more/less precise movement is achieved when deflection lever 44c articulates about axis 44d. For example, articulation of deflection lever 44c +/−45 degrees may cause the distal end 33a of endoscope 33 to deflect +370 degrees/−180 degrees. Thus, a unique calibration may be provided for each brand of endoscope 33. When the endoscope 33 is attached to the manipulator 31, the deflection lever 48 is placed inside the coupler 45 and precisely actuated. The deflection actuator 36 has a torque control and limiter to prevent any destruction of the deflection mechanism 110 tendon wires of the flexible endoscope 33.

In a non-limiting exemplary embodiment, as can be appreciated interchangeable holder 54 may be unique for each brand of endoscope 33. Such an interchangeable holder 54 can be retrofitted to provide alternate deflection ranges, as desired, for each brand of endoscope 33. For example, robotic manipulator 31 preferably has at least one endoscope holder 54, which is able to be attached to or detached from robotic arm 35. Therefore, different brands and models of flexible endoscopes 33 may be retrofitted with the robotic arm 35, without departing from the true spirit and scope of the present disclosure.

In a non-limiting exemplary embodiment, another precise motor 37a is placed in the laser fiber actuator 37 of the manipulator 31. That motor 37a moves the laser fiber forward and backward inside the working channel of flexible endoscope 33. The laser fiber is fixed with a special sterile adapter 47 and that adapter is placed in a fiber holder 46 of fiber actuator 37. That laser fiber actuator 37 and deflection actuator 36 are rotated together with flexible endoscope 33 by bent rotation actuator 35. As noted herein, actuating mechanism 112 may be retrofitted and employed with a variety of auxiliary instruments.

In a non-limiting exemplary embodiment, attached flexible endoscope 33 together with the laser fiber actuator 37 and the deflection actuator 36 are moved in the horizontal plane by way of a linear actuator inside actuator block 38. Such an actuator block 38 may be part of a cylindrical robot. Either one or two actuators can be used to move the flexible endoscope 33 with variable speed and longer displacement. The actuator block 38 moves the flexible endoscope 33 shaft inward/outward of the patient to perform the insertion/extraction movements of the flexible endoscope 33 according to forward/backward movement, respectively, of user handle 44b at the control console 40. To avoid looping or bending, the portion of the flexible endoscope 33 shaft is held (e.g., guided) by a length adjustable telescopic fixing rod 49.

In a non-limiting exemplary embodiment, all four mechanisms (i.e., horizontal movement 109, rotation 108, deflection 110 and laser fiber 112 movements) of the flexible endoscope 33 are fixed on top of a stable vertical lifting column 39. Such a lifting column 39 enables vertical movement of the flexible endoscope 33. That vertical movement is necessary to adjust a height of the flexible endoscope 33 to align the patient placed on the surgical table. Before starting the operation, the height should be adjusted according to the height of the access point of the patient.

In a non-limiting exemplary embodiment, after insertion of the flexible endoscope 33 into the patient, the flexible endoscope 33 is attached to the robotic manipulator 31. Then, the surgeon sits on the height adjustable and comfortable seat 41 of the control unit 32. The height and the distance to the surgeon's knees at the control unit 32 can be adjusted for ergonomics from the touch panel 50 of the console 40. The position settings according to the surgeon can be stored to memory for future usage. The surgeon can control all functions of the robotic manipulator 31 and all movements of flexible endoscope 33 from the control console 40 by either touch panel 50 and/or control handles 44*a*, 44*b*. The surgeon can control both fluoroscopy and laser operations by pressing at least one of the foot pedals 43. There is an optional video monitor 42 placed in front of the surgeon to show images from fluoroscopy or endoscopy camera unit(s). For example, it shows the video captured by the endoscopy camera, and switches to fluoroscopy images while the foot-pedal for fluoroscopy is pressed.

In a non-limiting exemplary embodiment, the advancement (e.g., distance) of the laser fiber is indicated on the touch panel screen 50 as the distance from distal end 33*a* of the flexible endoscope 33 to the tip of the laser fiber during the movements of laser fiber actuator 37. The software of the robotic manipulator 31 controls the emission of laser by controlling the foot pedal 40. Although the surgeon presses the foot pedal 43 for laser shooting, the control console 40 does not activate the laser if the tip of laser fiber is close to the distal end of flexible endoscope 33; thereby avoiding damage to the working channel of fURS 33.

In a non-limiting exemplary embodiment, system 30 includes at least one processor, and a memory in communication with the processor. The memory include software instructions (e.g., software program(s)), when executed by the processor, that cause the manipulator 31 to control movement of the fURS 33. Notably, such software instructions can control the fiber optic movements and deflection movements to achieve pre-defined movements. For example, it can precisely move the tip 33*a* of laser fiber like painting a picture for precise stone fragmentation/dusting by way of a Holmium YAG laser in the kidney. In addition, the software of the system 30 can control the horizontal (insertion) movement of the endoscope 33 for reduction of respiration effect (e.g., as the patient breaths, his/her body rises/falls during inhalation/exhalation).

In a non-limiting exemplary embodiment, the movements of the manipulator 31 have some pre-defined initial positions and the software controls all movements to achieve such initial positions according to the request of the surgeon from the control console 40. Such initial positions are defined in order to provide: a) easy access to the endoscope 33 and its working channel; b) safer insertion of laser fiber through a straight distal end 33*a* of endoscope 33; c) distance measurement of laser fiber; and d) a parking or storing position of the manipulator 31.

In a non-limiting exemplary embodiment, rotational movements and horizontal (insertion/extraction) movements originate from inside the actuator block 38. The lower plate 66 of horizontal movement is fixed on top of vertical lifting column 39. Highly precise horizontal movement is achieved by four linear ball bearings 53, 53*a* placed between lower 66 and upper 51 plates. Horizontal motion with variable speed is achieved by the precisely controlled stepper motor 65 and ball screw system 60, transferred by belt-pulley 64. Nut 63 of ball screw is connected to flange 61, which is fixed on the lower plate 66 in order to horizontally move the upper plate 51. Rotational movement is driven precisely by a DC motor 59 connected to a zero backlash speed reducer 57 through a motor flange 58. Such a zero backlash speed reducer 57 may be a conventional speed reducer, (e.g., a zero backlash CYCLO™ speed reducer) well-known in the industry. The speed of rotation is varied according to a corresponding operator rotation speed of handle 44*b* (e.g., according to operator input). The angle of rotation is measured by a rotational sensor 91 and its assembly 62. The output shaft of speed reducer 57 is connected to bent arm 35 through a bearing system 56 and a flange 55.

In a non-limiting exemplary embodiment, the system 30 has an irrigation pump 76 as an accessory. Such a pump 76 is a speed controlled peristaltic pump for pumping the irrigation saline through the working channel of flexible endoscope 33 thereby providing better vision and operation of laser lithotripsy. The flow rate is adjusted on touch panel interface 50 (e.g., user interface). Thus, the operator can turn on/off the pump from touch panel interface 50 at control console 40. In FIG. 7*a*, the irrigation pump 76 includes a peristaltic pump head 105, geared motor 77 (e.g., actuator) which actuates the pump head 105, a control printed circuit board interface 107 which controls the pump head 105 according to the signal coming from control console 40, and power supply unit 106.

In a non-limiting exemplary embodiment, the system 30 includes two primary components 31, 32, each having multiple elements. One component is control unit 32 where the surgeon provides user inputs for operating another component including a robotic manipulator 31, which holds and causes movements of a flexible endoscope 33.

In a non-limiting exemplary embodiment, the manipulator 31 has a holder 34 and 34*a* for easily fixing the commercially available flexible endoscope 33 into a rotation axis (e.g., x-axis 85). As a non-limiting example, the holder 34 may include a lever or a clamp 34*a* to tightly fix the endoscope 33 onto the holder 34.

In a non-limiting exemplary embodiment, when the hand piece of the flexible endoscope 33 is placed at the holder 34, the deflection lever 48 is placed inside the deflection coupler 45 of the manipulator 31.

In a non-limiting exemplary embodiment, a precise actuator 37 is engaged with the holder 46 and fiber fixing adapter 47, which squeezes the laser fiber and moves it inward or outward very precisely. That actuator 37 is moved together with the hand piece of flexible endoscope 33.

In a non-limiting exemplary embodiment, the surgeon can move the flexible endoscope 33 forward and backward along the horizontal (first) axis inside the patient body either by moving the manipulator 31 in a corresponding horizontal direction relative to the stationary patient table, or by moving the patient table in corresponding horizontal direction relative to the stationary manipulator 31.

The system 30 enables the operator to make a variety of maneuvers of the flexible endoscopes such as: concentric rotation about an axis (e.g., x-axis 85) shaft and hand-piece of flexible endoscope 33; deflection of the distal end 33*a* of endoscope 33; the precise movement of laser fiber inward to outward inside the working channel of flexible endoscope 33; and the horizontal movement of the endoscope 33 forward/backward with a desired speed; and the vertical movement of endoscope 33 as up/down.

In a non-limiting exemplary embodiment, the surgeon may remotely make all maneuvers from the control console 40. There are two handles 44*a*, 44*b* for providing three exemplary movements of the flexible endoscope 33. One of the handles 44*a* is for deflection movement. Such a handle 44*a* is shaped like the real flexible endoscope 33 hand piece to enable faster adaptation of the surgeon and has a deflection lever 44*c* for controlling the deflection of the distal part 33*a* of the flexible endoscope 33. Deflection lever 44*c* is pivotal about fulcrum axis 44*d* and realistically receives tensional resistance from timing belt 74, which simulates external forces acting on the distal part 33*a* (e.g., distal portion of the insertion tube) of the endoscope 33. In this manner, the realistic feedback at deflection handle 44a is similar to a haptic feedback that provides a real-time sense of touch.

In a non-limiting exemplary embodiment, deflection lever 44c transfers a user input via timing belt 74. Notably, the elasticity of time belt 74 imparts a frictional resistance at lever 44c. Thus, the user receives a realistic touch and/or motion feedback (e.g., haptic feedback) similar to directly holding/operating the endoscope 33. Such realistic feedback simulates a tendon-type movement of the flexible endoscope 33. For example, sensor 92 detects the external force acting at the distal part 33a and notifies the electro-magnetic brake 73 to rotate more/less quickly, thereby simulating a life-like tensional feeling on the endoscope 33 deflection handle 44a when movement of the distal end 33a is restricted (e.g., engaged, contacted, etc.) by the organs or other objects. In addition, to control deflection lever 44c movement for deflecting the distal part 33a, wheel 71 is employed to precisely control such pivotal movement about axis 44d.

In a non-limiting exemplary embodiment, the other handle 44b controls both the rotational and the horizontal movements. The rotation control is actuated by rotating handle 44b, the horizontal movement is actuated by linearly reciprocating handle 44b forward and backward.

The control console 40 of the system 30 is user friendly and ergonomic. The height of the seat 41 and control console 40 can be adjusted according to the surgeon. In addition, the distance between control console 40 and the knee of the user can be adjusted. The adjusted positions of the seat 41 and control console 40 can be stored into/reloaded from the memories labeled by the names of surgeons for future uses.

In a non-limiting exemplary embodiment, a video monitor 42 can be connected in front of the user to show images from a fluoroscopy or an endoscopy camera unit. Normally, it shows the video of the endoscopy camera (e.g., located at the end of the fiber endoscope or digital camera placed on the tip of video endoscope), it shows the fluoroscopy images while the foot-pedal for fluoroscopy is pressed. In case the user prefers to use his/her own video monitor of the endoscopy camera and the fluoroscopy camera, then the video monitor 42 of the control console 40 can be removed.

In a non-limiting exemplary embodiment, the control console 40 enables the surgeon to select the deflection mode of the fURS 33 as either European style (Lever Up/Tip Down-Lever Down/Tip Up) or US style (Lever Up/Tip Up-Lever Down/Tip Down) by pressing related buttons on the screen.

In a non-limiting exemplary embodiment, the control console 40 is equipped with a touch screen control device with menu-operated software. The menus on the control screen are user-friendly and exemplary functions are grouped as separate titles including: deflection movement, rotational movement, horizontal movement, vertical movement, laser fiber movement, and irrigation pump discharge.

Regarding the vertical movement, the surgeon can adjust the height of fURS 33 and its holder 34, thereby displaying a height value from a floor to the rotation axis (e.g., x-axis 85). Regarding the horizontal movement, the surgeon can select the speed of horizontal movement. The horizontal movement value is displayed numerically and graphically. In addition, there are controls for moving the fURS 33 to predetermined positions. Regarding the laser fiber movement, the surgeon can move the laser fiber forward and backward by pressing the controls and, the distance from the tip of fURS 33 to the tip of laser fiber is displayed numerically and graphically. There are two controls (e.g., touch screen buttons) for moving the laser fiber to an initial position and a firing position where the fiber tip is seen on camera.

Regarding the rotational movement, the rotation angle of the fURS 33 is displayed numerically and graphically. The graphical indication of the rotation angle is also displayed on the video monitor 42 overlaid by the camera view or the camera image is rotated according to the rotation angle. There is also one button to rotate the fURS 33 holder 34 to a desired position for connecting the fURS 33 thereto.

Regarding the deflection movement, the deflection angle of the fURS 33 is displayed numerically and graphically. There is a button to straighten the tip of fURS 33 for introducing the laser fiber inside the working channel of the fURS 33. There are also two buttons for selecting the deflection mode of the fURS 33 as either European or US style.

Regarding the irrigation pump operation, the surgeon can select the speed of the irrigation pump and can start/stop the pump 76 and can flush the irrigation pump 76 (e.g., pumping by maximum speed) by pressing the related buttons.

In a non-limiting exemplary embodiment, the manipulator 31 is robotically operated and designed to hold commercially available flexible endoscopes and further enables a user (e.g., operator, surgeon, etc.) to remotely maneuver the endoscope 33 in a variety of directions during extended operating procedures. As a non-limiting example, the robotic manipulator 31 can rotate the flexible endoscope 33 about its longitudinal central axis (e.g., x-axis 85), move it forward and backward, deflect as well as move the laser fiber forward and backward within the working channel of flexible endoscope 33.

In a non-limiting exemplary embodiment, one purpose of the remotely-operated robotic control system 30 is to hold the flexible endoscope 33 and to make the all maneuvers remotely for long-duration operations. In this manner, the surgeon can sit down to control the robotic manipulator 31 (endoscope, laser fiber, etc.) outside of a radiation-exposed area near the patient and control all movements of the robotic manipulator 31 to make the treatment via the fURS 33.

In a non-limiting exemplary embodiment, the remotely-operated robotic control system 30 preferably includes two parts. One part is the control unit 32 where the surgeon sits and controls all maneuvers of flexible endoscope 33. The second part is the robotic manipulator 31 which holds and makes all necessary movements of flexible endoscope 33.

The remotely-operated robotic control system 30 enables the surgeon to maneuver the flexible endoscopes 33 in a variety of directions. As a non-limiting example, the endoscope 33 can be concentrically rotated relative to a longitudinal axis of the hand-piece and a shaft of the flexible endoscope 33. As a non-limiting example, the distal end of the endoscope 33 can be deflected as needed. As a non-limiting example, the laser fiber can be precisely moved along an inward-to-outward direction, and visa-versa, inside the working channel of the flexible endoscope 33 (e.g., via 37, 37a, 46, and 47). As a non-limiting example, the endoscope 33 may be horizontally displaced along a forward-to-backward direction, and visa-versa. As a non-limiting example, the endoscope 33 may be vertically displaced along an up/down direction.

Non-limiting exemplary benefits of the present disclosure include the following: a) enables a surgeon to perform treatments having longer duration; b) keeps the surgeon away from X-ray radiation area; c) enables the surgeon to manipulate the flexible endoscope 33 by sitting on the control unit 40 without becoming exhausted because of wearing lead aprons and holding the endoscope 33 in a standing position for a long operation time; d) reduces the time of operation by means of keeping the endoscope 33 in stable position and has a lower probability of missing the target in the organ because of reduction in surgeon's concentration, or changing hands for different procedures such as insertion laser fiber into a working channel of endoscope 33; e) reduces the time operation and increases the success by use of pre-defined movements to achieve special functions such as painting like movements or popcorn techniques for the fragmentation/dusting of the stone in kidney, which provides precise and fast operation; f) increases the life of the flexible endoscope 33 by reducing the risks of damaging the flexible endoscope 33 (e.g., controls the emission of laser to avoid any laser emission near to the distal end of the endoscope 33, and it controls the deflection actuator 36 and it makes the distal end 33a of endoscope 33 in the straight position before insertion of laser fiber in to the working channel to avoid the perforation of the working channel by the tip of the laser fiber); g) enables the surgeon to release his hands from the control handles 44a, 44b without losing the position of the endoscope 33 from the target inside the body of patient; h) reduces the learning period to use flexible endoscope 33 by enabling the surgeon to manipulate all movements of flexible endoscope 33 by user-friendly handles 44a, 44b by easier instructions; and, i) allows remote simulation training for the flexible endoscope 33.

Referring to FIGS. 12-20b, a plurality of flowcharts illustrate control logic algorithms of software instructions employed by a non-limiting exemplary embodiment of the present disclosure. Various steps of the flowcharts are identified by a single capital letter such as R, C, D, L, H, I, V, etc. Such steps preferably identify a return point after a series of preceding steps of performed. For example, such steps may mean that the user interface returns to an initial prompt screen or to the beginning of a category within a high-level menu.

Figure 12:
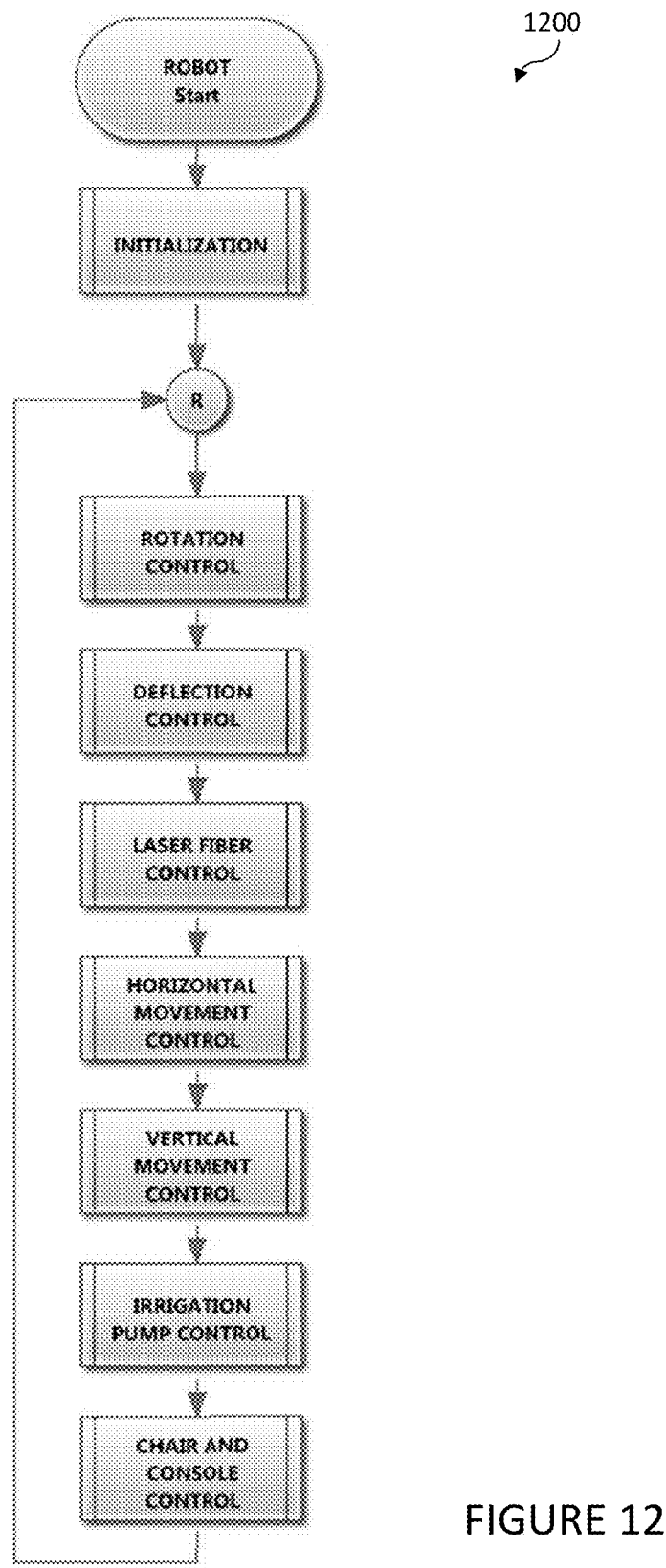
FIG. 12 is a flowchart illustrating a series of manipulator control functions that can be actuated by an operator.
Figure 13:
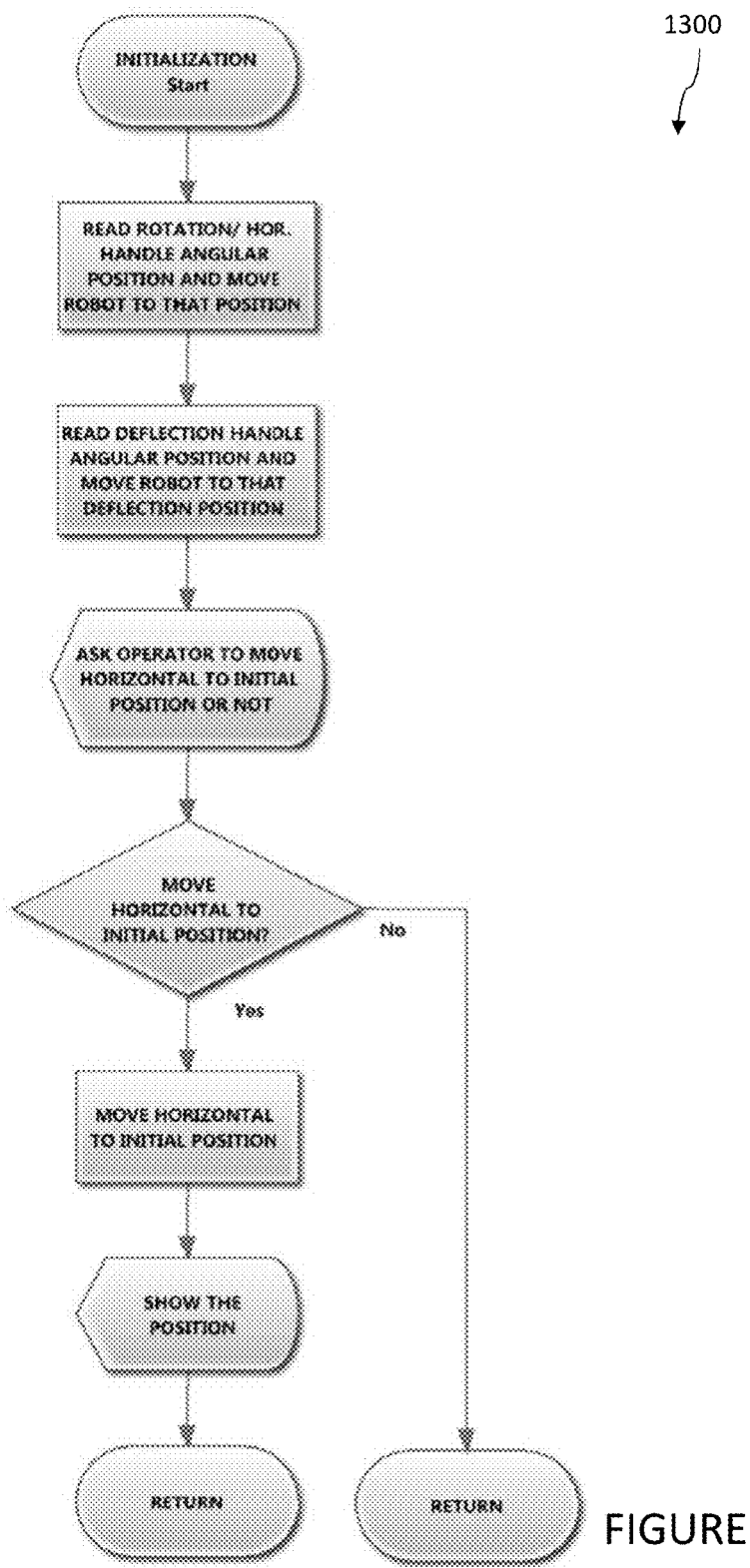
FIG. 13 is a flowchart illustrating a series of steps for initializing a position of the manipulator regarding rotational movement, horizontal movement and deflection movement.
Figure 14:
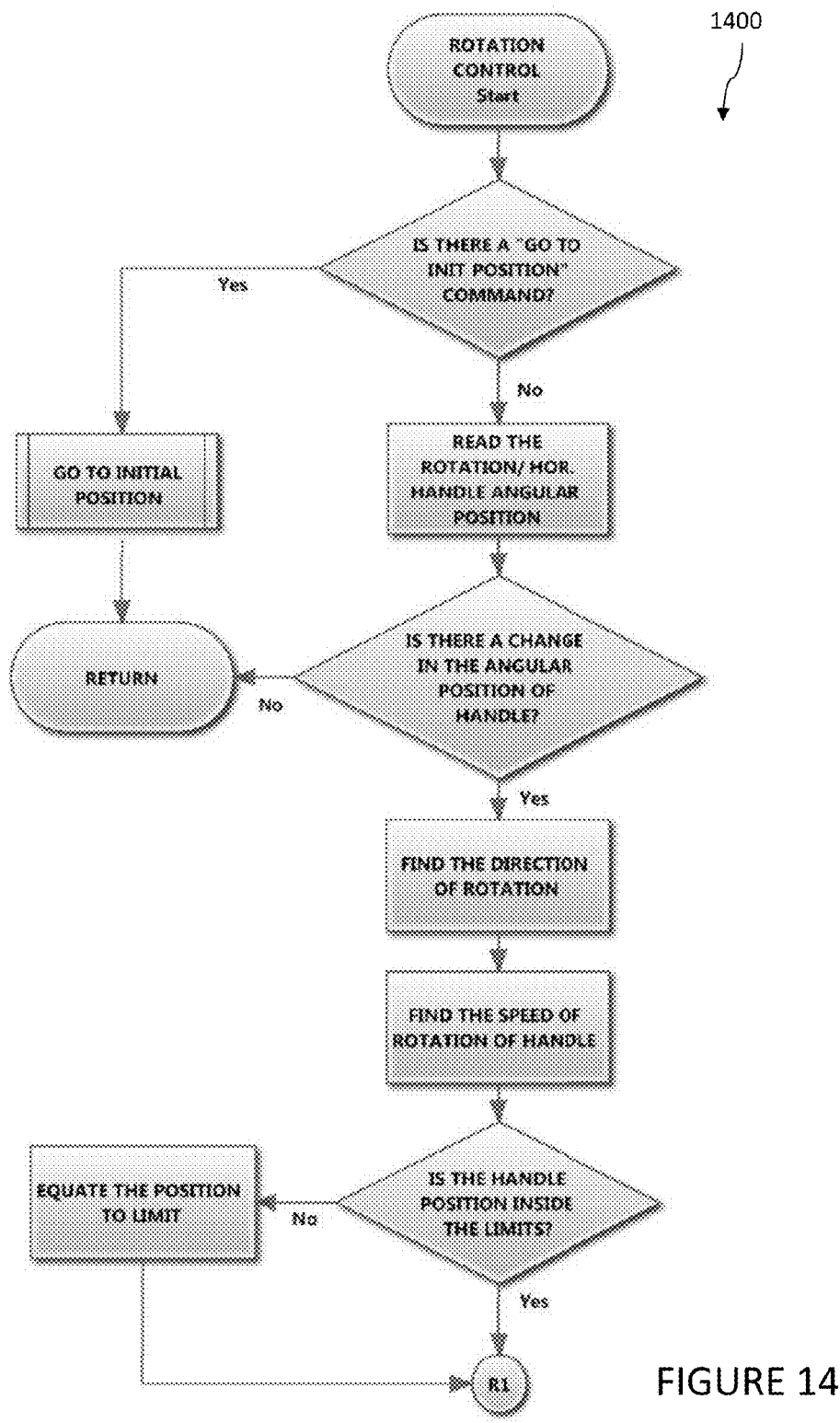
FIGS. 14-14a are flowcharts illustrating a series of steps for maneuvering the rotation mechanism according to learned angular and speed displacements of the control handles.
Figure 14A:
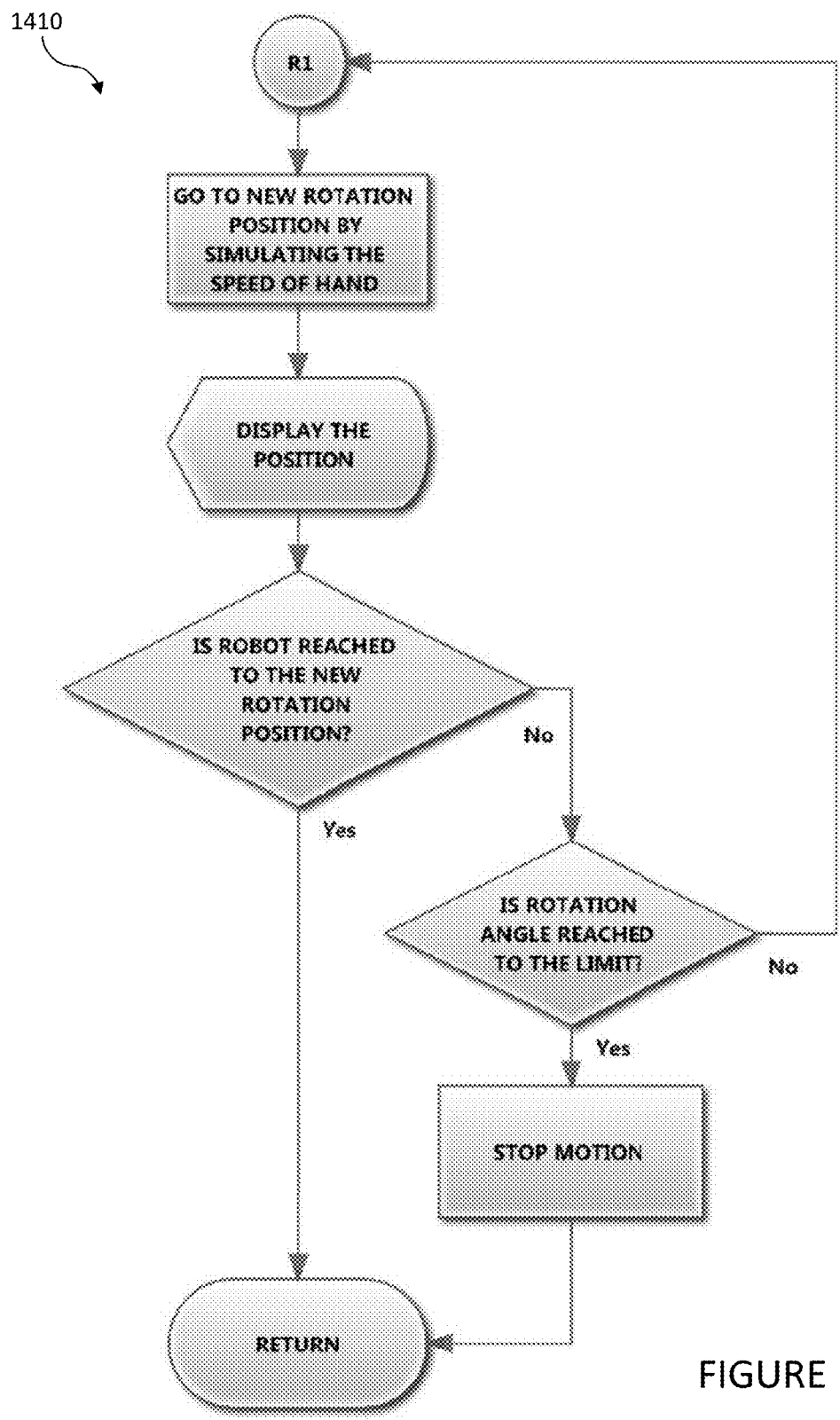
Figure 15:
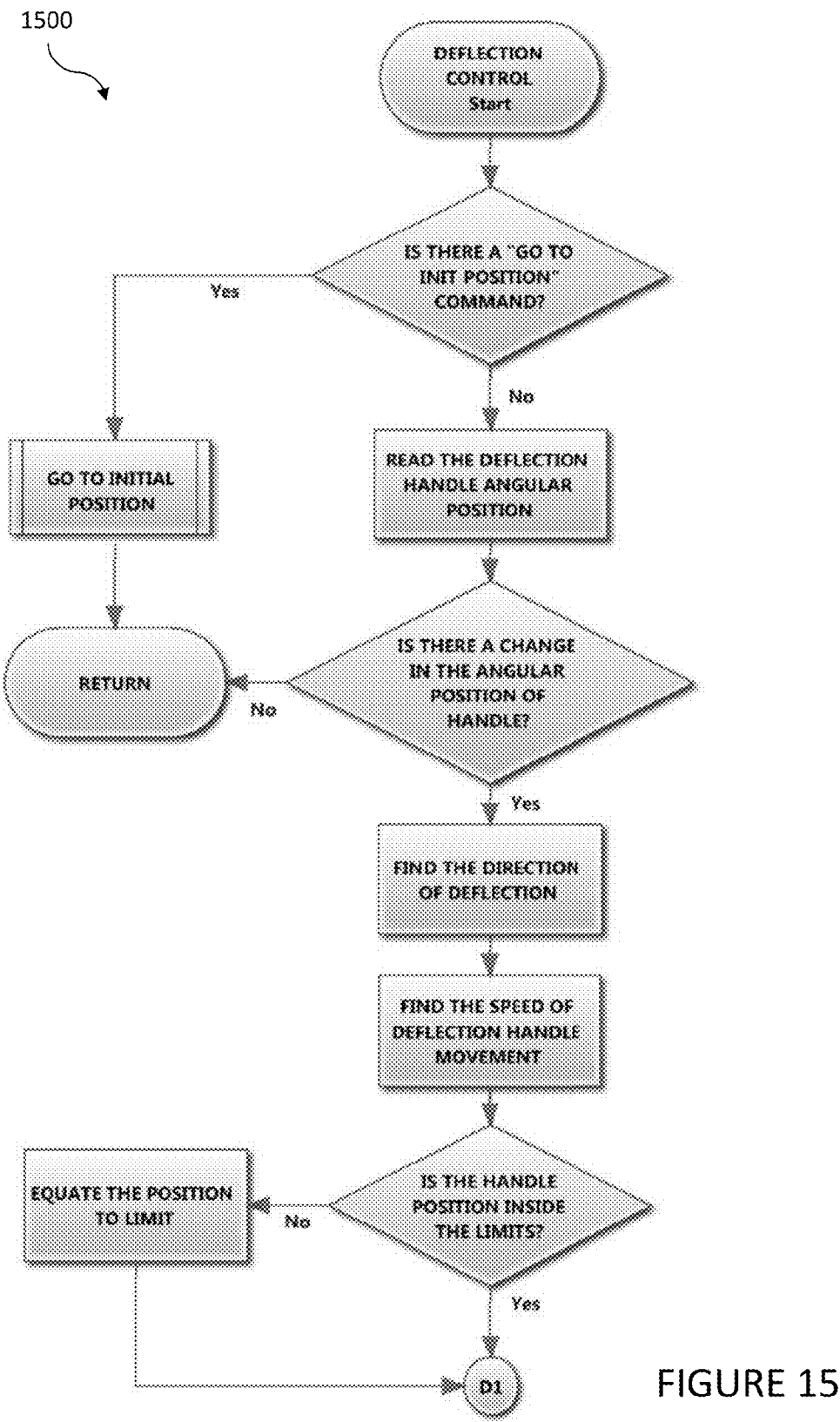
FIGS. 15-15a are flowcharts illustrating a series of steps for maneuvering the deflection mechanism according to learned angular and speed displacements of the control handles.
Figure 15A:
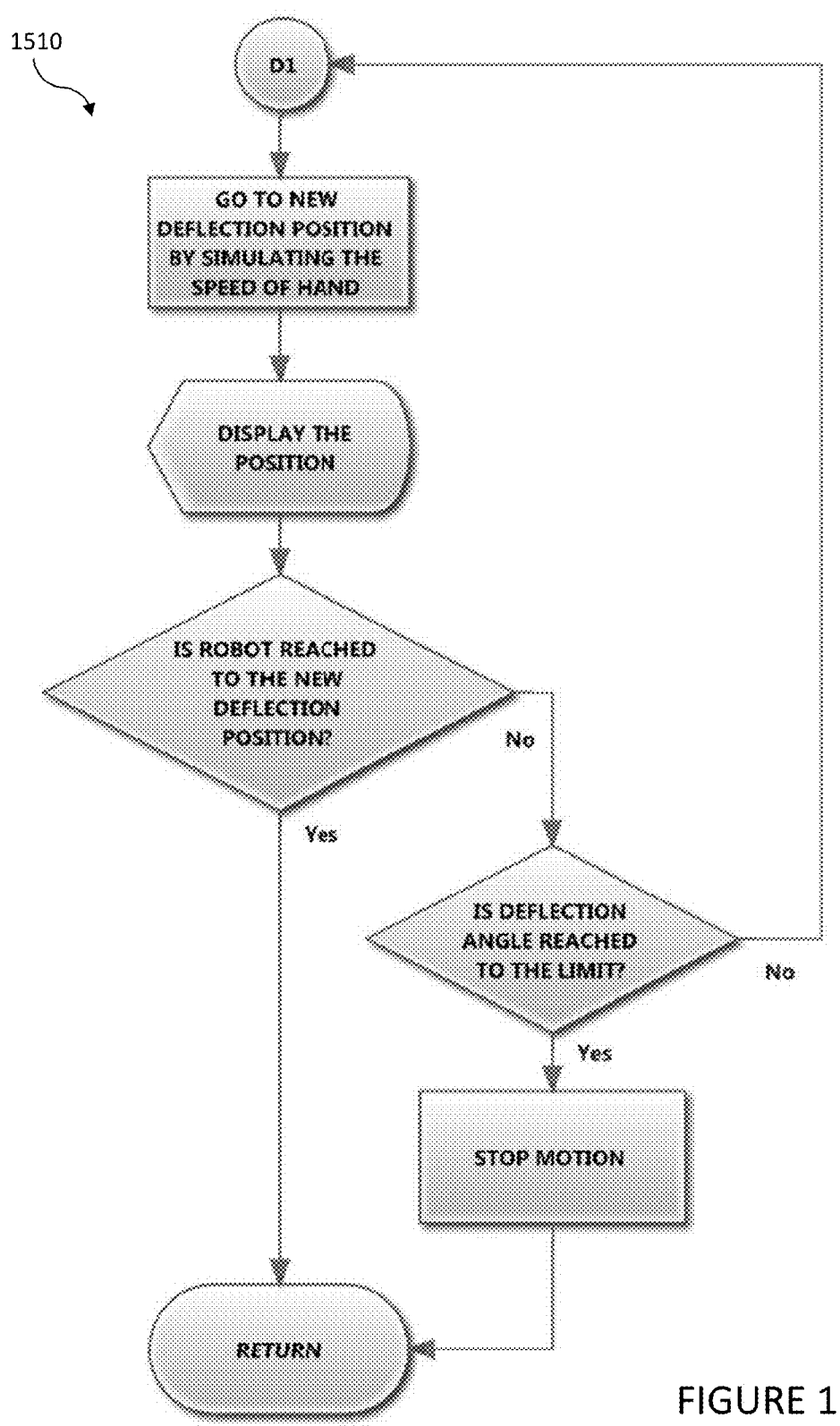
Figure 16:
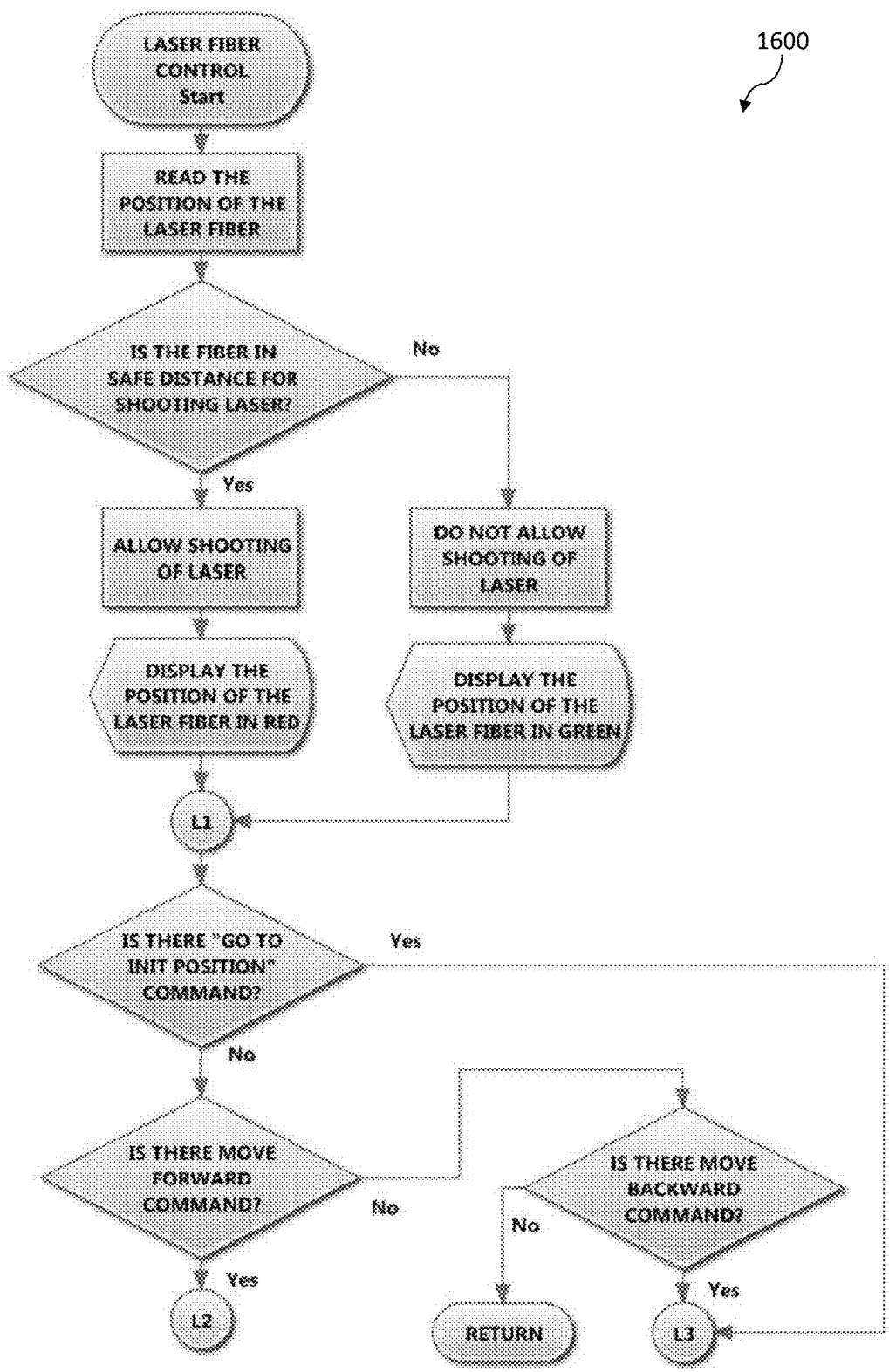
FIGS. 16-16a are flowcharts illustrating a series of steps for maneuvering the auxiliary instrument (e.g., laser fiber) actuating mechanism according to a learned position of the laser fiber relative to the working channel of the flexible endoscope.
Figure 16A:
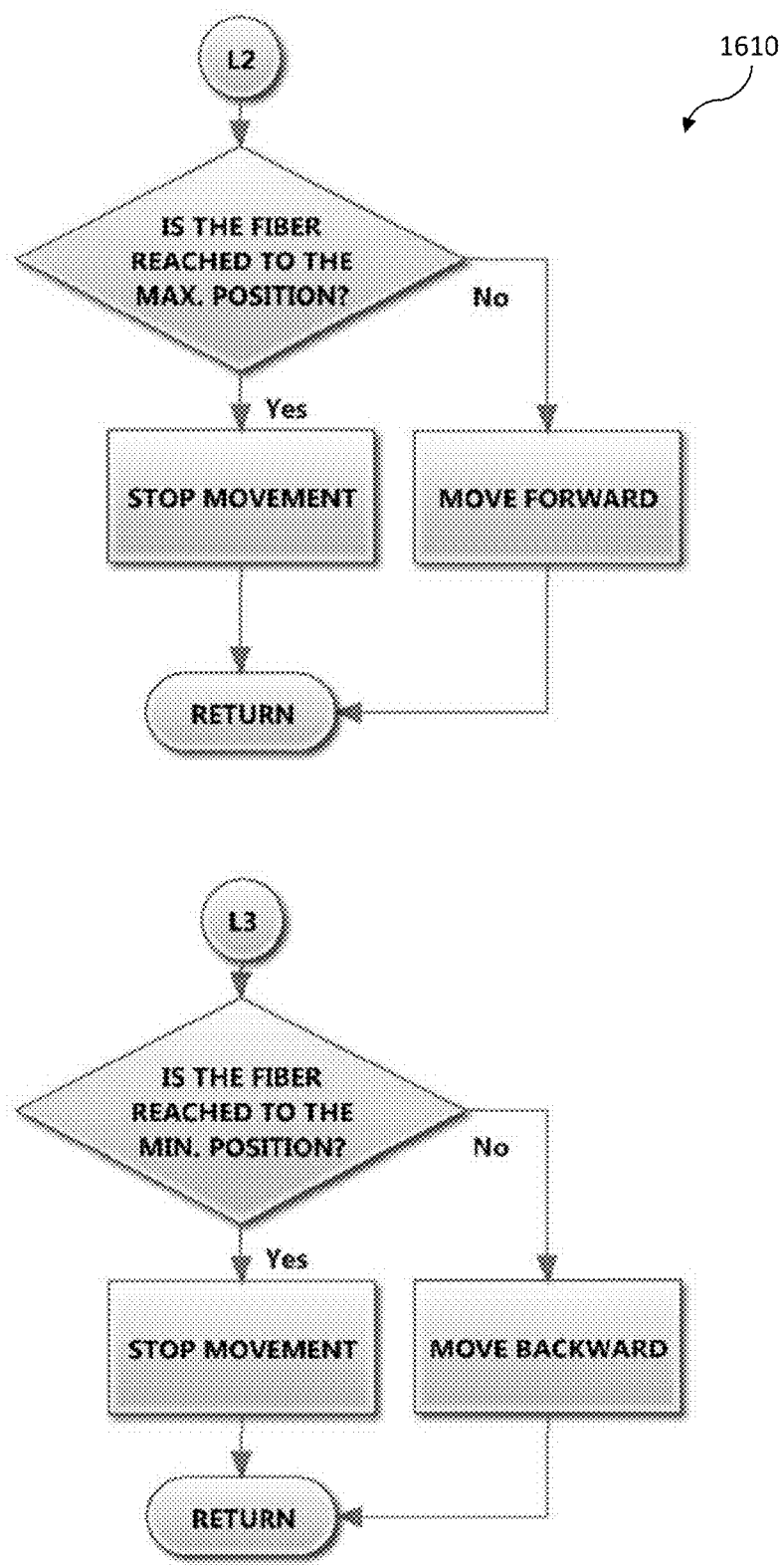
Figure 17:
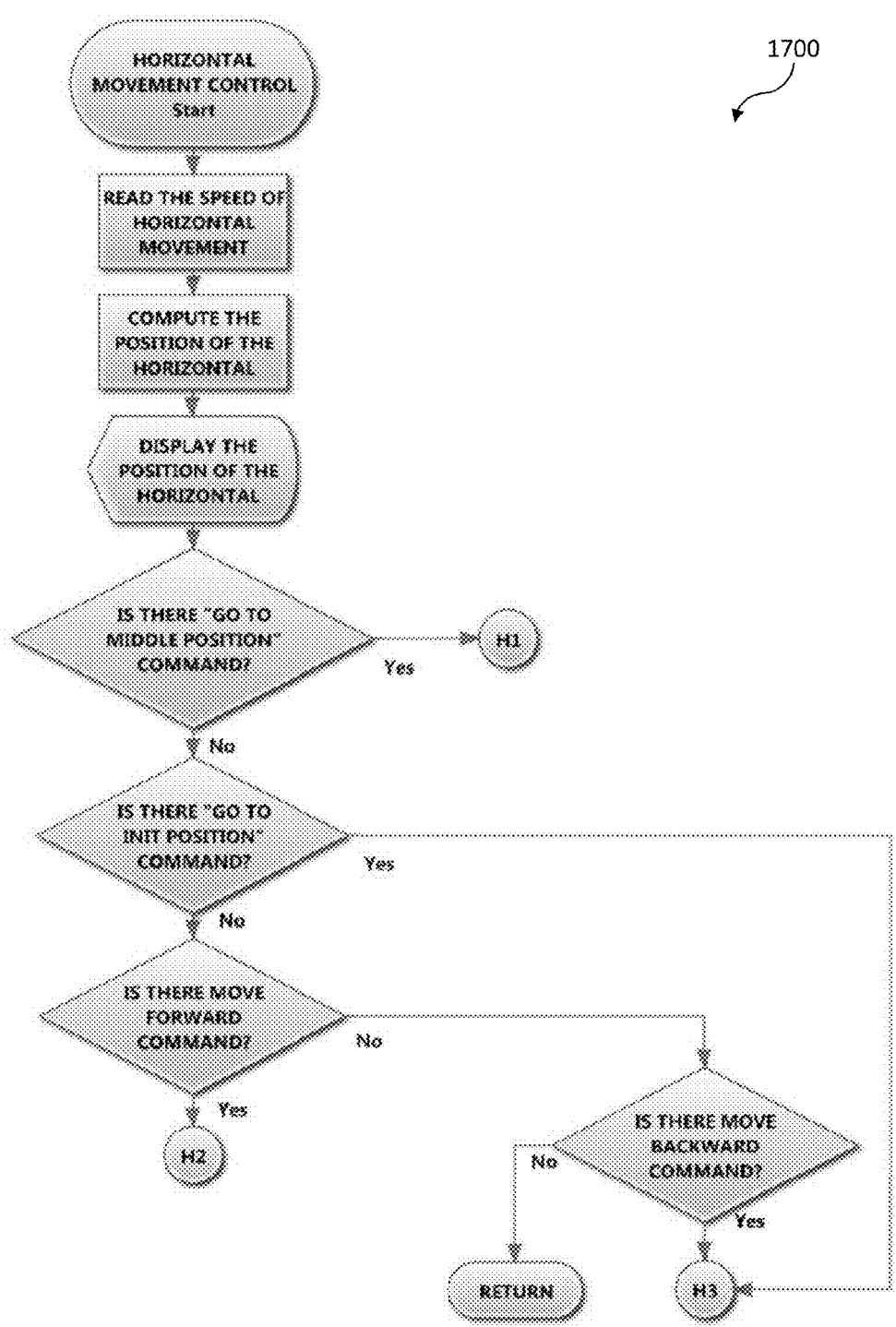
FIGS. 17-17a are flowcharts illustrating a series of steps for maneuvering the horizontal movement mechanism thereby displacing either the manipulator or the patient bed along a horizontal path.
Figure 17A:
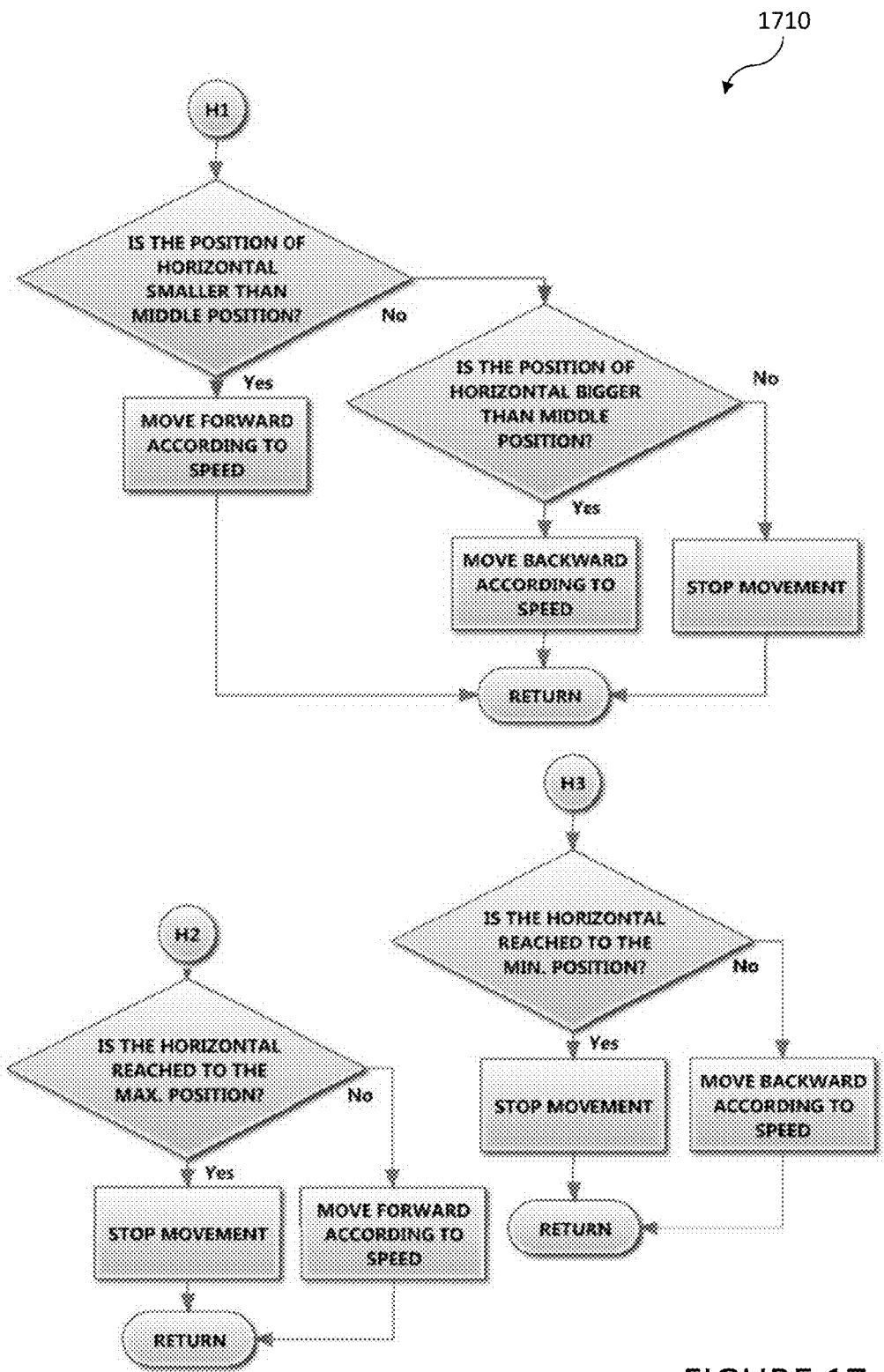
Figure 18:
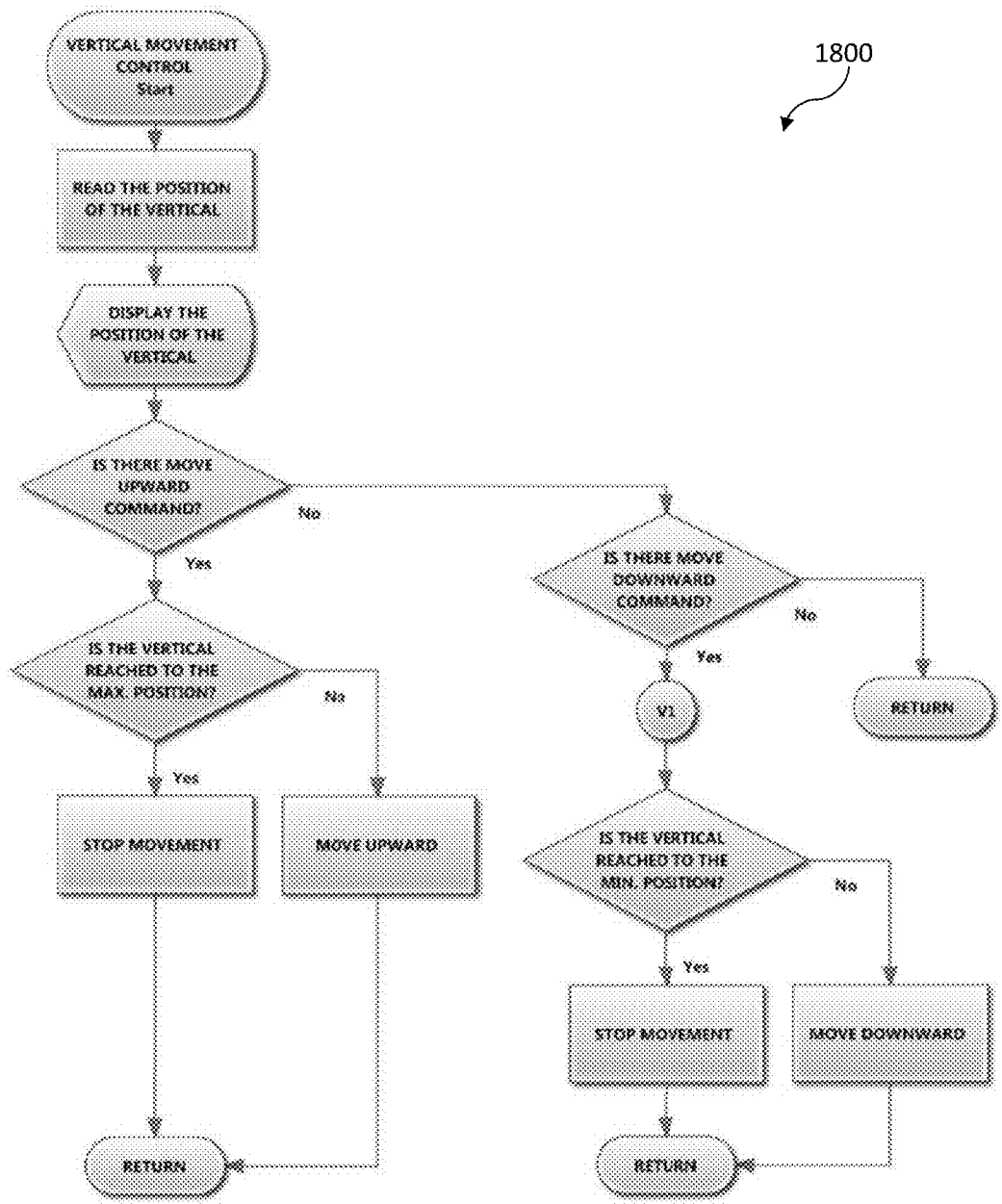
FIG. 18 is a flowchart illustrating a series of steps for maneuvering the vertical movement mechanism and thereby displacing the manipulator along a vertical path.
Figure 19:
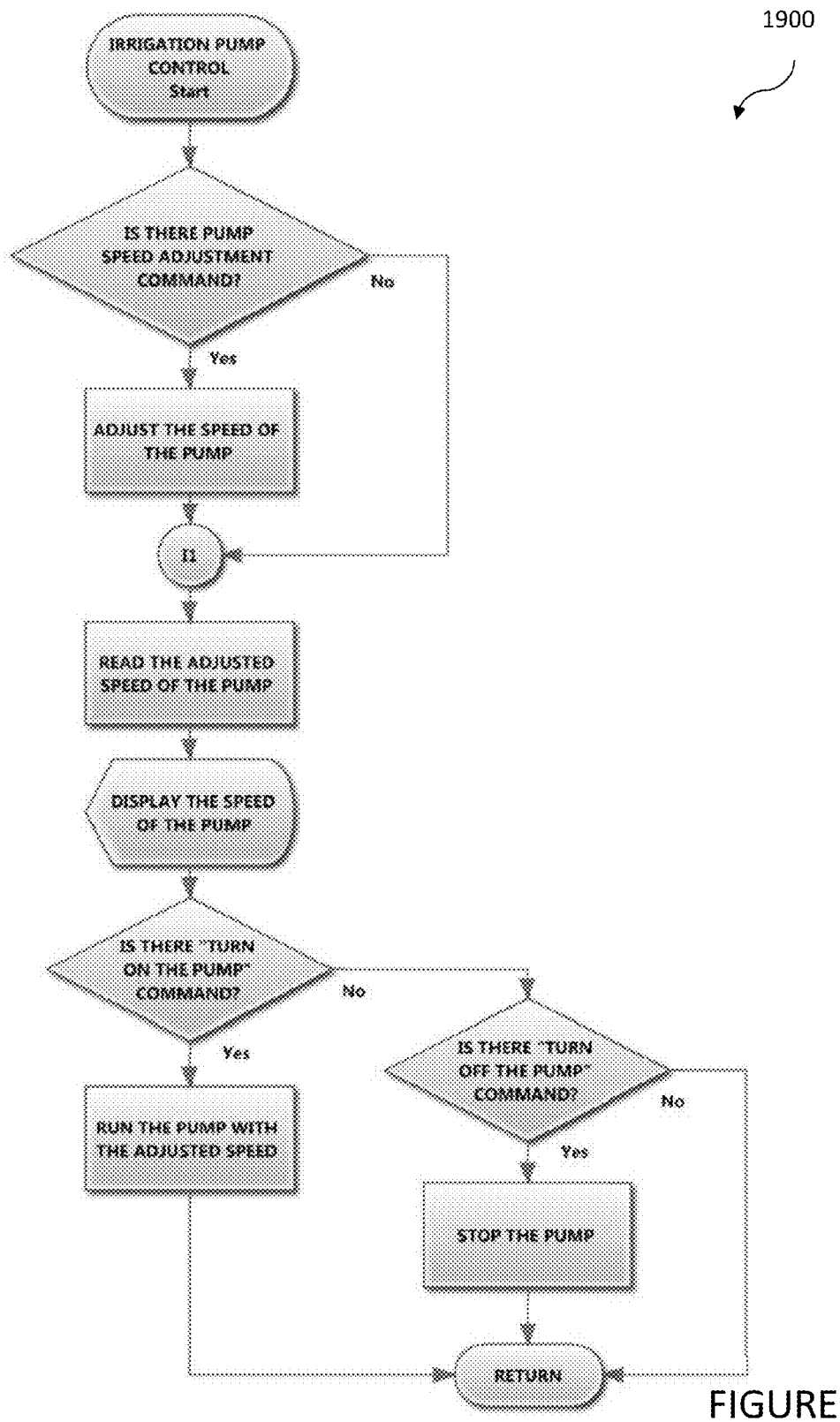
FIG. 19 is a flowchart illustrating a series of steps for maneuvering the irrigation pump actuating mechanism located at the manipulator.
Figure 20:
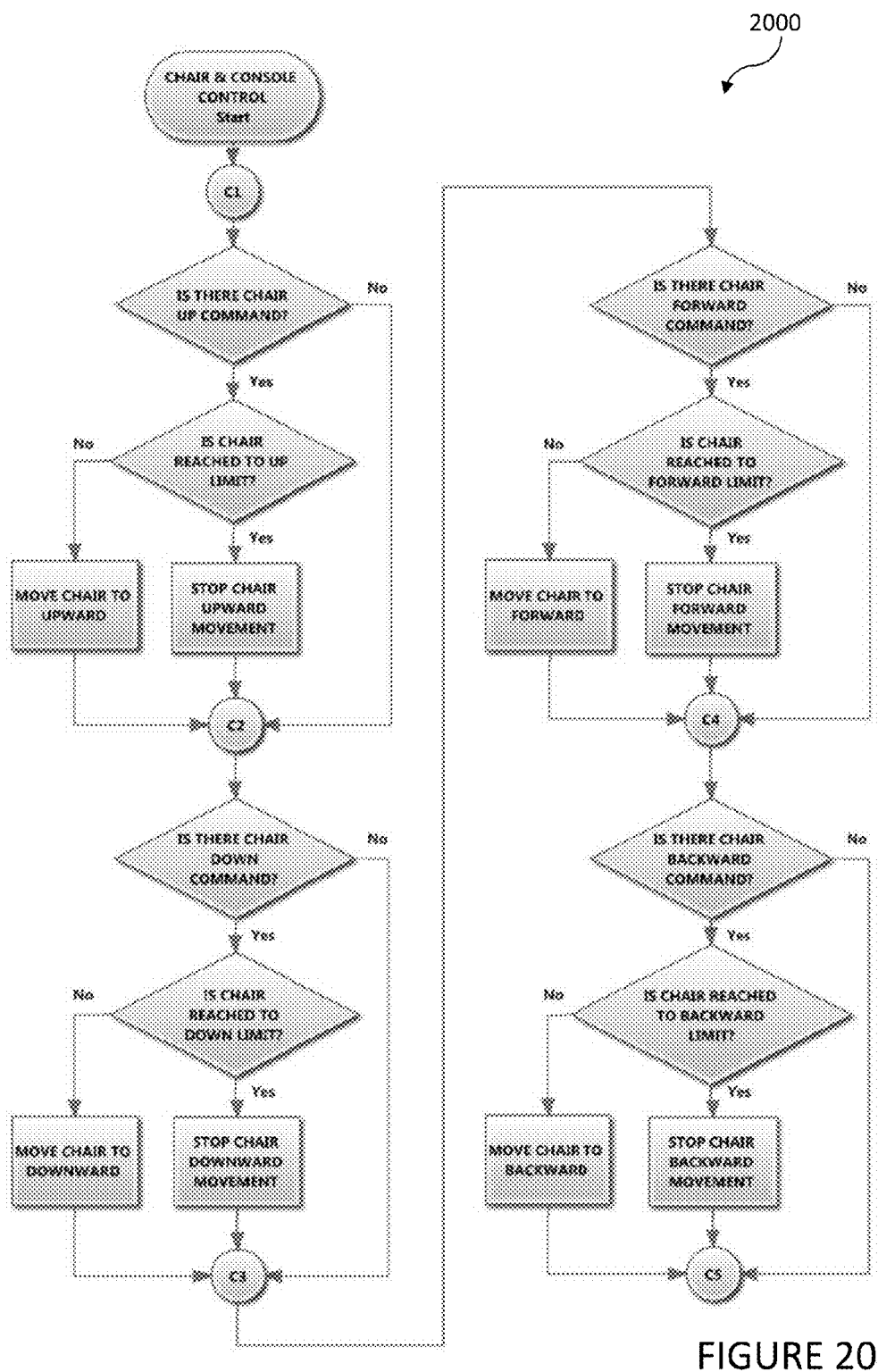
FIGS. 20-20b are flowcharts illustrating a series of steps for maneuvering the vertical movement mechanism and thereby displacing various portions of the control console along a vertical path.
Figure 20A:
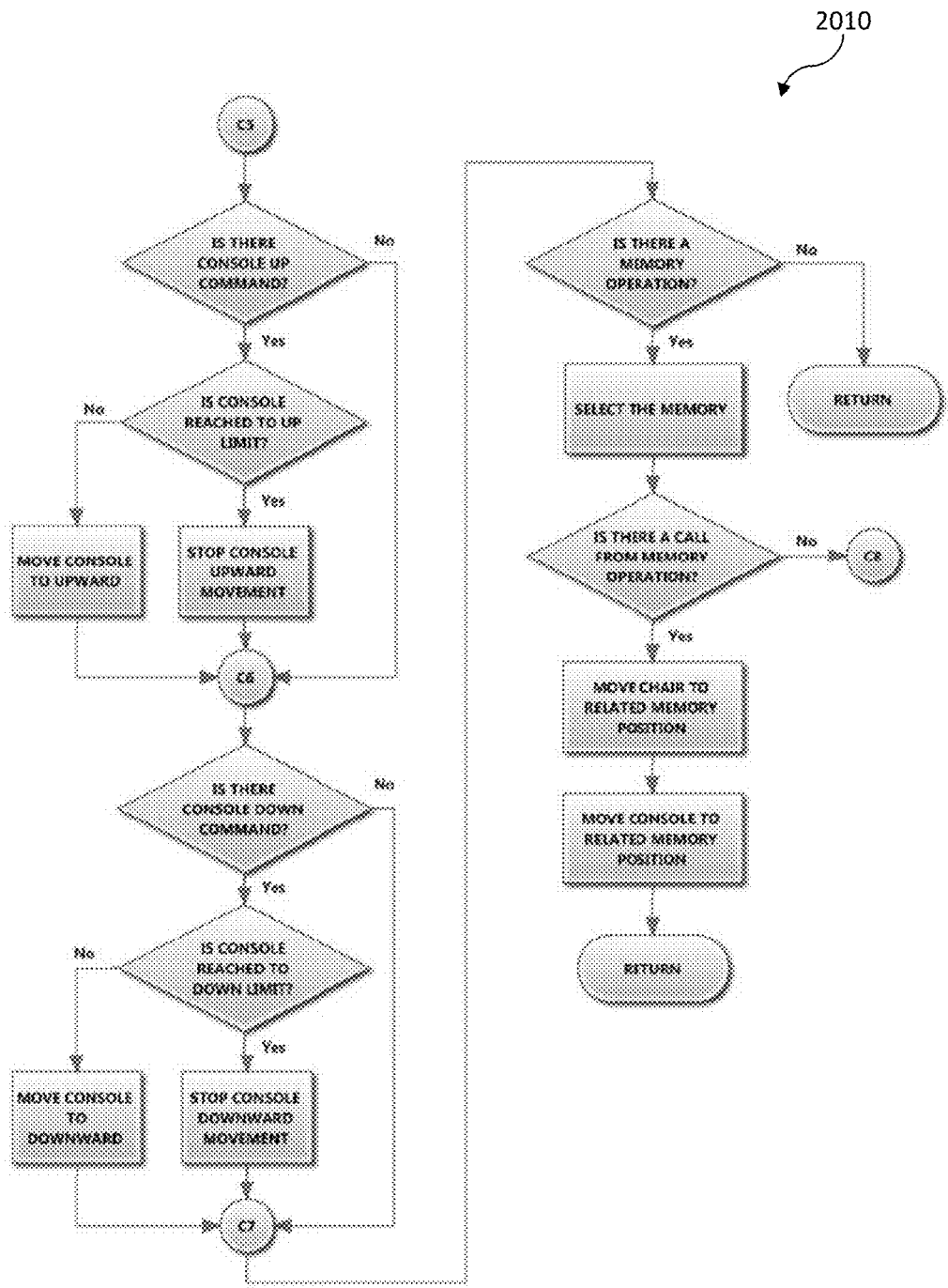
Figure 20B:
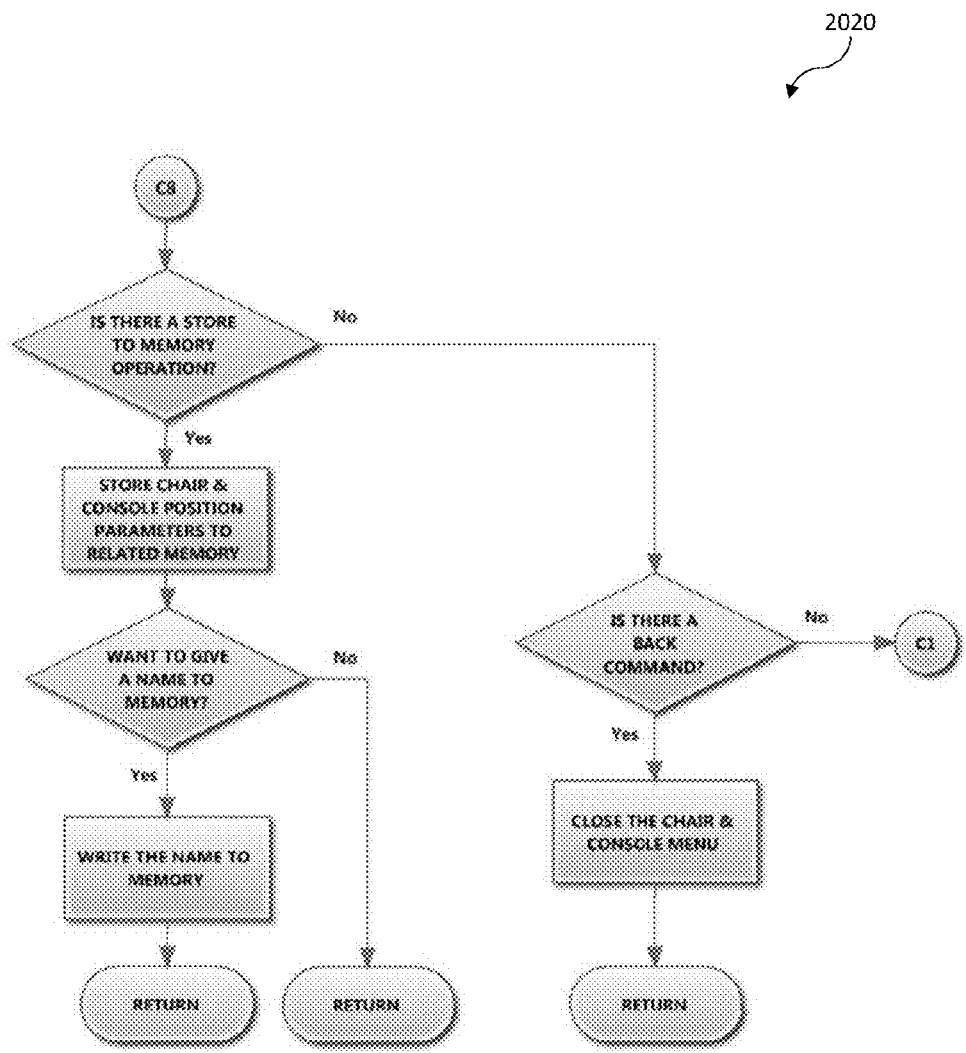

In a non-limiting exemplary embodiment, FIG. 12 is a flowchart 1200 illustrating a series of control functions that can be actuated by an operator. FIG. 13 is a flowchart 1300 illustrating a series of steps for initializing a position of the robot regarding rotational movement, horizontal movement and deflection movement. FIGS. 14-14a are flowcharts 1400, 1410 illustrating a series of steps for maneuvering the rotation mechanism 108 according to learned angular and speed displacements of the control handles. FIGS. 15-15a are flowcharts 1500, 1510 illustrating a series of steps for maneuvering the deflection mechanism 110 according to learned angular and speed displacements of the control handles. FIGS. 16-16a are flowcharts 1600, 1610 illustrating a series of steps for maneuvering the laser fiber actuating mechanism 112 according to a learned position of the laser fiber. FIGS. 17-17a are flowcharts 1700, 1710 illustrating a series of steps for maneuvering the horizontal movement mechanism 109 thereby displacing either the manipulator 31 or the patient bed along a horizontal path. FIG. 18 is a flowchart 1800 illustrating a series of steps for maneuvering the vertical movement mechanism 111 and thereby displacing the manipulator 31 along a vertical path. FIG. 19 is a flowchart 1900 illustrating a series of steps for maneuvering the irrigation pump controller (actuating mechanism) at the manipulator 31. FIGS. 20-20b are flowcharts 2000, 2010, 2020 illustrating a series of steps for maneuvering the vertical movement mechanism 111 and thereby displacing various portions of the control console along a vertical path.

Controllers (e.g., 31, 32) employed by non-limiting exemplary embodiment(s) of the present disclosure, may include a processor such as a microprocessor or other devices capable of being programmed or configured to perform computations and instruction processing in accordance with the disclosure. Such other devices may include microcontrollers, digital signal processors (DSP), Complex Programmable Logic Device (CPLD), Field Programmable Gate Arrays (FPGA), application-specific integrated circuits (ASIC), discrete gate logic, and/or other integrated circuits, hardware or firmware in lieu of or in addition to a microprocessor.

Functions and process steps described herein may be performed using programmed computer devices and related hardware, peripherals, equipment and networks. When programmed, the computing devices are configured to perform functions and carry out steps in accordance with principles of the disclosure. Such programming may comprise operating systems, software applications, software modules, scripts, files, data, digital signal processors (DSP), application-specific integrated circuit (ASIC), discrete gate logic, or other hardware, firmware, or any conventional programmable software, collectively referred to herein as a module.

Memory employed by the present disclosure may include programmable software instructions that are executed by the processor. In particular, the programmable software instructions include a plurality of chronological operating steps that define a control logic algorithm for performing the intended functions of the present disclosure. Such software instructions may be written in a variety of computer program languages such as C++, Fortran and Pascal, for example. One skilled in the art understands that such software instructions may contain various Boolean logic processes that perform the intended function of the present disclosure. Therefore, the specific source or object code of the software program is not intended to be a limiting factor in executing the present disclosure's intended function.

The memory, which enables storage of data and programs, may include RAM, ROM, flash memory and any other form of readable and writable storage medium known in the art or hereafter developed. The memory may be a separate component or an integral part of another component such as processor.

In accordance with various embodiments, the methods (e.g., horizontal movement, rotational movement, deflectional movement, vertical movements, etc.) described herein may be implemented as one or more software programs running on a computer processor. Dedicated hardware implementations including, but not limited to, application specific integrated circuits, programmable logic arrays and other hardware devices can likewise be constructed to implement the methods described herein. Further, alternative software implementations including, but not limited to, distributed processing or component/object distributed processing, parallel processing, or virtual machine processing can also be constructed to implement methods described herein.

It should also be noted the software that implements the disclosed methods (e.g., functions, movements, etc.) may optionally be stored on a tangible storage medium, such as a magnetic medium, such as a disk or tape; a magneto-optical or optical medium, such as a disk; or a solid state medium, such as a memory card or other package that houses one or more read-only (non-volatile) memories, random access memories, or other re-writable (volatile) memories. The software may also utilize a signal containing computer instructions. A digital file attachment to e-mail or other self-contained information archive or set of archives is considered a distribution medium equivalent to a tangible storage medium. Accordingly, the disclosure is considered to include a tangible storage medium or distribution medium as listed herein, and other equivalents and successor media, in which the software implementations herein may be stored.

Referring back to FIG. 22, it is noted that a variety of communication protocols may operably link the control unit 32 to the manipulator 31. By way of example and not limitation, a communications device at the control unit 31 may communicate with a communications device at the manipulator 31 using one or more wireless LAN (WLAN) protocols, using low power, ultra wide band (UWB) communication signals or some other type of wireless signals for RF or optical (e.g., infrared) communication of information to maneuver the rotational mechanism 108, horizontal movement mechanism 109, deflection mechanism 110, vertical movement mechanism 111, laser fiber actuating mechanism 112, irrigation pump actuating mechanism 113, etc. A real-time WLAN protocol or a standard wireless LAN protocol such as that of IEEE 802.11.times., Bluetooth or IrDA may be used without departing from the scope of the present disclosure. A local network that connects the communications devices to their respective local computer systems may, for example, include a single, unified full duplex LAN, such as a 100BaseT Ethernet LAN. Alternatively, the local network may include two or more interconnected LANs or other network communications means. Any of a variety of other types of computer systems and associated applications may be provided on the network.

Optionally, various ports and interfaces may be provided to communicate with peripherals, subsystems and systems. Such devices may include serial ports for bi-directional communications, and/or an optical communications (e.g., infrared) port for wireless line of sight communications. Other ports may include parallel and USB ports.

In an exemplary embodiment, the communications devices facilitate digital communications between system components, such as the control unit 31 and manipulator 31. The communications devices may include, but are not limited to, Ethernet 100 baseT, RS232, USB, and other serial communications modules. Optionally, the devices could be implemented as a wireless communications component operating according to a wireless communication protocol, such as 802.11 or IRDA.

In addition to having a communications module, which may employ RS232, RS422, Ethernet, 802.11, IRDA, or any other protocol used to exchange data between the control unit 32 and the manipulator 31, each communications device may have a microcontroller, which acts as a protocol converter for conversion between a protocol used to communicate with the control unit 32, and a protocol used to communicate with the manipulator 31. In other embodiments, the microcontroller could be another PC, or even a separate process, such as a process that communicates through a PCI interface board. The microcontroller may have an internal clock oscillator that provides a time base for all serial communication operations. Alternatively, a crystal and associated circuitry may be utilized for a timing base. Those skilled in the art will appreciate that any device capable of timing and controllably directing data from stored memory to output pins for communication in a compatible format to the manipulator 31 could be used and is intended to come within the scope of the disclosure.

In addition, wireless communication according to one implementation of the present disclosure may comprise radio frequency (RF), optical and/or acoustic communication equipment, employing any well-known wireless communication media, techniques and protocols now known in the art or later available.

In a non-limiting exemplary embodiment, the control unit 32 may communicate with the manipulator 31 via one of more standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same or similar functions as those disclosed herein are considered equivalents thereof.

The display screen 42 is configured for displaying various amounts of textual and/or graphical information. The display may be monochrome or color, of various physical dimensions, of various types. In one embodiment, the display may be suitable for displaying full motion video in color. By way of example and not limitation, the display may be comprised of a liquid crystal display (LCD); a field emission display FED; so called "E-ink" technologies, which employ microspheres having at least two reflectance states; a cathode-ray tube (CRT) display; a gas plasma display; an LED readout configured to display alpha-numeric and graphical information; or any other compatible visual display device. In a preferred implementation, the display is large enough to display, with clarity, one or more lines of information. Preferably, the display screen is configured with a touch-screen interface, to present a user with a graphical user interface.

It is noted that although a control unit 32 is illustrated for receiving and transmitting a user input to maneuver the manipulator 31, various control environments may be employed without departing from the true scope of the present disclosure. For example, a web-based user interface and/or hand-actuated portable controller (e.g., gesture recognition device) may be employed to receive and transmit the user input. Such a web-based user interface may reside at an electronic device (e.g., mobile phones, handhelds, home appliances, set top boxes, PC, laptop, etc.), which includes browser software. In such browser-enabled devices, the user interface and control architecture is implemented using the browser software (i.e., a browser-based interface and control architecture) rather than a full-function operating system (O/S). An advantage is that the manipulator 31 may be remotely accessed via a web-based application that can be simultaneously viewed by multiple users, while a primary user (e.g., operator) generates user input for maneuvering the manipulator 31. Such a control environment at least greatly reduces the need for the control console 32 depicted herein.

While non-limiting exemplary embodiment(s) has/have been described with respect to certain specific embodiment(s), it will be appreciated that many modifications and changes may be made by those of ordinary skill in the relevant art(s) without departing from the true spirit and scope of the present disclosure. It is intended, therefore, by the appended claims to cover all such modifications and changes that fall within the true spirit and scope of the present disclosure. In particular, with respect to the above description, it is to be realized that the optimum dimensional relationships for the parts of the non-limiting exemplary embodiment(s) may include variations in size, materials, shape, form, function and manner of operation.

The Abstract of the Disclosure is provided to comply with 37 C.F.R. § 1.72(b) and is submitted with the understanding that it will not be used to interpret or limit the scope or meaning of the claims. In addition, in the above Detailed Description, various features may have been grouped together or described in a single embodiment for the purpose of streamlining the disclosure. This disclosure is not to be interpreted as reflecting an intention that the claimed embodiment(s) require more features than are expressly recited in each claim. Rather, as the following claims reflect, inventive subject matter may be directed to less than all of the features of any of the disclosed non-limiting exemplary embodiment(s). Thus, the following claims are incorporated into the Detailed Description, with each claim standing on its own as defining separately claimed subject matter.

The above disclosed subject matter is to be considered illustrative, and not restrictive, and the appended claims are intended to cover all such modifications, enhancements, and other embodiment(s) which fall within the true spirit and scope of the present disclosure. Thus, to the maximum extent allowed by law, the scope of the present disclosure is to be determined by the broadest permissible interpretation of the following claims and their equivalents, and shall not be restricted or limited by the above detailed description.

What is claimed as new and what is desired to secure by Letters Patent of the United States is:

1. A manipulator for maneuvering a flexible uretero-renoscope to a desired location within a target zone, said manipulator comprising:
    at least one controller;
    a rotation mechanism in communication with said at least one controller and being rotated about a first axis;
    a horizontal movement mechanism in communication with said at least one controller and being displaced along a first path; and
    a deflection mechanism capable of receiving a portion of the flexible uretero-renoscope, said deflection mechanism being in communication with said at least one controller and displaced along a second path;
    wherein displacement of said deflection mechanism along said second path causes deflection of a distal end of the flexible uretero-renoscope;
    wherein said deflection mechanism is located exterior of said rotation mechanism and spaced therefrom such that said second path is spaced and axially offset from said rotation mechanism;
    wherein said rotation mechanism is rotated about said first axis independently of displacement of said deflection mechanism along said second path;
    wherein each of said deflection mechanism and rotation mechanism is spaced proximally from the distal end of the flexible uretero-renoscope;
    wherein said deflection mechanism includes a holder interchangeable with a plurality of different ones of the flexible uretero-renoscope.

2. The manipulator of claim 1, wherein said second path travels about a second axis registered substantially perpendicular to said first axis.

3. The manipulator of claim 2, wherein said first axis is an x-axis and said second axis is a y-axis, wherein said second path has an arcuate curvature defined along a plane parallel to a z-axis.

4. The manipulator of claim 1, wherein said first path is linear and registered substantially parallel to said first axis.

5. The manipulator of claim 1, wherein said first path is non-overlapping and mutually exclusive of said second path.

6. The manipulator of claim 1, wherein said deflection mechanism is independently operable from each of said horizontal movement mechanism and said rotation mechanism.

7. The manipulator of claim 1, wherein said deflection mechanism is contemporaneously operable with each of said horizontal movement mechanism and said rotation mechanism.

8. The manipulator of 1, further comprising: a vertical movement mechanism in communication with said at least one controller and configured to raise and lower said rotation mechanism and said deflection mechanism along a third path registered substantially orthogonal to said first path.

9. The manipulator of claim 1, further comprising: an auxiliary instrument actuating mechanism in communication with said at least one controller and attached to said deflection mechanism and located proximate to said horizontal movement mechanism.

10. A robotic control system for maneuvering a flexible uretero-renoscope to a desired location within a target zone during a medical procedure, said robotic control system comprising:
    a control unit capable of receiving an operator input; and
    a manipulator in communication with said control unit and responsive to said operator input, said manipulator including
    at least one controller,
    a rotation mechanism in communication with said at least one controller and being rotated about a first axis,
    a horizontal movement mechanism in communication with said at least one controller and being displaced along a first path,
    a deflection mechanism capable of receiving a portion of the flexible uretero-renoscope, said deflection mechanism being in communication with said at least one controller and being displaced along a second path;
    wherein displacement of said deflection mechanism along said second path causes deflection of a distal end of the flexible uretero-renoscope;
    wherein said rotation mechanism and said deflection mechanism are simultaneously rotated about said first axis; and
    an actuator block;
    wherein each of said rotation mechanism and said horizontal movement mechanism is housed at said actuator block;
    wherein said deflection mechanism is located exterior of said actuator block;
    wherein each of said deflection mechanism and rotation mechanism is spaced proximally from the distal end of the flexible uretero-renoscope;
    wherein at least one of said deflection mechanism and said rotation mechanism engages said actuator block;
    a display device in communication with said control unit;
    wherein said manipulator further includes a robotic arm having at least one laser fiber actuator for actuating a laser fiber, said laser fiber actuator including
        a laser fiber connection adapter,
        at least one laser fiber holder for holding said laser fiber connection adapter, and
        at least one movement unit for moving said at least one laser fiber holder with respect to the flexible uretero-renoscope;
    wherein an advancement distance of the laser fiber is indicated on said display device as a distance from a distal end of the flexible uretero-renoscope to a tip of said laser fiber during movement of said laser fiber actuator;
    wherein said robotic manipulator includes a foot pedal and software to control emission of laser radiation, wherein the software is configured to disable the emission of laser radiation if the tip of the laser fiber is closer than a predetermined distance from the distal end of the flexible uretero-renoscope;

wherein said deflection mechanism includes a holder interchangeable with a plurality of different ones of the flexible uretero-renoscope.

11. The robotic control system of claim 10, wherein said second path travels about a second axis registered substantially perpendicular to said first axis.

12. The robotic control system of claim 11, wherein said first axis is an x-axis and said second axis is a y-axis, wherein said second path has an arcuate curvature defined along a plane parallel to a z-axis.

13. The robotic control system of claim 10, wherein said first path is linear and registered substantially parallel to said first axis.

14. The robotic control system of claim 10, wherein said first path is non-overlapping and mutually exclusive of said second path.

15. The robotic control system of claim 10, wherein said deflection mechanism is independently operable from each of said horizontal movement mechanism and said rotation mechanism.

16. The robotic control system of claim 10, wherein said deflection mechanism is contemporaneously operable with each of said horizontal movement mechanism and said rotation mechanism.

17. The robotic control system of 10, further comprising: a vertical movement mechanism in communication with said at least one controller and configured to raise and lower said rotation mechanism and said deflection mechanism along a third path registered substantially orthogonal to said first path.

18. The robotic control system of claim 10, further comprising: an auxiliary instrument actuating mechanism in communication with said at least one controller and attached to said deflection mechanism and located proximate to said horizontal movement mechanism.

19. The robotic control system of claim 10, further comprising: an irrigation pump actuating mechanism in communication with said control unit and being responsive to said user input for selectively discharging fluid into a working channel of the flexible uretero-renoscope.

20. A method of utilizing a robotic control system for maneuvering a flexible uretero-renoscope to a desired location within a target zone during a medical procedure, said method comprising the steps of:

obtaining a control unit capable of receiving an operator input;

obtaining and communicating a manipulator with said control unit wherein said manipulator is responsive to said operator input, said manipulator including at least one controller, a rotation mechanism in communication with said at least one controller and being rotated about a first axis, a horizontal movement mechanism in communication with said at least one controller and being displaced along a first path, and a deflection mechanism capable of receiving a portion of the flexible uretero-renoscope wherein said deflection mechanism is in communication with said at least one controller and displaced along a second path;

providing an actuator block;

housing each of said rotation mechanism and said horizontal movement mechanism is at said actuator block;

locating said deflection mechanism exterior of said actuator block;

displacing said deflection mechanism along said second path thereby causing deflection of a distal end of the flexible uretero-renoscope; and simultaneously rotating said rotation mechanism and said deflection mechanism about said first axis;

wherein each of said deflection mechanism and rotation mechanism is spaced proximally from the distal end of the flexible uretero-renoscope;

wherein at least one of said deflection mechanism and said rotation mechanism engages said actuator block;

wherein said deflection mechanism is located exterior of said rotation mechanism and spaced therefrom such that said second path is spaced and axially offset from said rotation mechanism;

wherein said rotation mechanism is rotated about said first axis independently of displacement of said deflection mechanism along said second path;

wherein said deflection mechanism includes a holder interchangeable with a plurality of different ones of the flexible uretero-renoscope.

* * * * *